(12) United States Patent
Fallin et al.

(10) Patent No.: US 7,150,757 B2
(45) Date of Patent: Dec. 19, 2006

(54) ADJUSTABLE LINE LOCKS AND METHODS

(76) Inventors: T. Wade Fallin, 210 E. 200 South, Hyde Park, UT (US) 84318; Kwan-Ho Chan, 4803 1st Pl., Lubbock, TX (US) 79416-3149; Margaret Mary Sinnott, 1755 Country Club Dr., Logan, UT (US) 84321

( * ) Notice: Subject to any disclaimer, the term of this patent is extended or adjusted under 35 U.S.C. 154(b) by 489 days.

(21) Appl. No.: 10/459,375

(22) Filed: Jun. 11, 2003

(65) Prior Publication Data

US 2004/0254593 A1 Dec. 16, 2004

(51) Int. Cl.
*A61B 17/04* (2006.01)

(52) U.S. Cl. .................. 606/232; 606/74; 606/103; 24/129 R

(58) Field of Classification Search ............ 606/232, 606/74, 103; 24/115 R, 129 R, 130, 129 B, 24/129 W
See application file for complete search history.

(56) References Cited

U.S. PATENT DOCUMENTS

| | | | |
|---|---|---|---|
| 1,452,338 A | | 4/1923 | Flowers |
| 1,806,162 A | * | 5/1931 | Hahn .................. 24/129 B |
| 2,441,336 A | | 5/1948 | Sova |
| 3,409,014 A | | 11/1968 | Shannon |
| 3,678,543 A | | 7/1972 | Hobbs |
| 3,715,782 A | | 2/1973 | Newell |
| 3,785,009 A | | 1/1974 | Nysten |
| 3,880,166 A | | 4/1975 | Fogarty |
| 3,910,281 A | | 10/1975 | Kletschka |
| 3,976,079 A | | 8/1976 | Samuels |
| 4,034,443 A | | 7/1977 | Turner |
| 4,105,349 A | | 8/1978 | Kupperman et al. |
| 4,280,435 A | | 7/1981 | Loomis |
| 4,477,947 A | | 10/1984 | Lyons |
| 4,480,357 A | | 11/1984 | Cummins |
| 4,480,358 A | | 11/1984 | Barling |
| 4,646,394 A | | 3/1987 | Krauss |
| 4,785,509 A | | 11/1988 | Fisher |
| 4,831,692 A | | 5/1989 | Chaun |
| 4,910,834 A | | 3/1990 | Minkler |

(Continued)

FOREIGN PATENT DOCUMENTS

GB 2 046 826 A 11/1980

(Continued)

OTHER PUBLICATIONS

Abstract of Japanese application No. 04286884, published Apr. 26, 1994.

*Primary Examiner*—Julian W. Woo
(74) *Attorney, Agent, or Firm*—Medicinelodge, Inc.; David W. Meibos; Daniel F. Justin

(57) ABSTRACT

A line lock includes a body at least partially bounding a primary passageway, a secondary passageway, and a working passageway. In one embodiment at least a portion of the working passageway is disposed between the primary passageway and the secondary passageway such that a geometric line segment extending between the primary passageway and the secondary passageway intersects with working passageway. A line extends through the primary passageway, the secondary passageway and then through the working passageway such that a relative compression section of the line is formed between the primary passageway and the secondary passageway. The compression section of the line selectively biases against a portion of the line extending out of the working passageway so as to selectively lock the line to the body when the line is tensioned against the body.

63 Claims, 14 Drawing Sheets

U.S. PATENT DOCUMENTS

| | | |
|---|---|---|
| 4,932,962 A | 6/1990 | Yoon |
| 4,976,013 A | 12/1990 | Wax |
| 5,074,874 A | 12/1991 | Yoon |
| 5,123,913 A | 6/1992 | Wilk |
| 5,210,911 A * | 5/1993 | Brown et al. ............. 24/129 B |
| 5,284,485 A | 2/1994 | Kammerer |
| 5,403,330 A | 4/1995 | Tuason |
| 5,445,167 A | 8/1995 | Yoon et al. |
| 5,527,341 A | 6/1996 | Gogolewski |
| 5,572,770 A | 11/1996 | Boden |
| D376,095 S | 12/1996 | Curtis |
| 5,601,557 A | 2/1997 | Hayhurst |
| 5,630,824 A | 5/1997 | Hart |
| 5,653,719 A | 8/1997 | Raiken |
| 5,693,060 A | 12/1997 | Martin |
| 5,725,556 A | 3/1998 | Moser |
| 5,741,281 A | 4/1998 | Martin |
| 5,741,301 A | 4/1998 | Pagedas |
| 5,752,964 A | 5/1998 | Mericle |
| 5,759,189 A | 6/1998 | Ferragamo |
| 5,769,894 A | 6/1998 | Ferragamo |
| 5,782,864 A | 7/1998 | Lizardi |
| 5,839,768 A | 11/1998 | Wackerly |
| 5,891,168 A | 4/1999 | Thal |
| 5,931,855 A | 8/1999 | Buncke |
| 5,950,284 A | 9/1999 | Persson |
| 6,024,758 A | 2/2000 | Thal |
| 6,030,007 A | 2/2000 | Bassily |
| 6,045,574 A | 4/2000 | Thal |
| 6,066,160 A | 5/2000 | Colvin et al. |
| 6,095,282 A | 8/2000 | Sadeck |
| 6,106,545 A | 8/2000 | Egan |
| 6,132,439 A | 10/2000 | Kontos |
| 6,171,317 B1 | 1/2001 | Jackson et al. |
| 6,319,271 B1 | 11/2001 | Schwarts |
| 6,432,123 B1 | 8/2002 | Schwarts |
| 6,485,065 B1 | 11/2002 | Lusk et al. |
| 6,652,561 B1 | 11/2003 | Tran |
| 2002/0123758 A1 | 9/2002 | Buchman |
| 2004/0098053 A1 | 5/2004 | Tran |

FOREIGN PATENT DOCUMENTS

| | | |
|---|---|---|
| JP | 6-114067 | 4/1994 |

* cited by examiner

ADJUSTABLE LINE LOCKS AND METHODS

CROSS-REFERENCE TO RELATED APPLICATIONS

Not applicable.

BACKGROUND OF THE INVENTION

1. The Field of the Invention

The present invention relates generally to devices to replace knots and more specifically to devices to replace surgical knots tied in open, arthroscopic, and endoscopic procedures.

2. The Relevant Technology

Numerous devices have been developed to eliminate the need to tie knots as a way of securing a line. The devices that accomplish the same function as a knot, which is in part to secure a line to retain tension in a portion of the line, are typically referred to as line locks.

Line locks generally operate in one of two ways. Some line locks are manually actuated to secure one or more lines so that tension is maintained in a portion of the line(s). Once actuated, the line lock resists sliding along the line(s) either toward or away from the tensioned portion of the line. Other line locks are continuously adjustable in one direction so that tension is increased in the portion of the line upon which the line lock is advanced. The continuously adjustable line locks resist movement away from the tensioned portion of the line, but can be further advanced toward the tensioned portion of the line with an appropriately applied force.

The portion of a line that is put under tension, typically to secure some object, is commonly referred to as the standing end. The portion of the line that extends toward the line handler is commonly referred to as the working end. A knot in a line, or a line lock attached to a line, is the demarcation between the standing end and the working end.

Continuously adjustable line locks offer several advantages. They are passive locking devices, meaning that no other operation is required to secure the line lock once it is moved along the line to its desired position. Furthermore, these line locks can be used to continuously increase the tension in the standing end until it reaches a desired level of tension.

The advantages of line locks over tied knots are very attractive in many varied applications, including the use of surgical sutures. However, the line locks developed to date have many deficiencies when considered for surgical suture applications. For example, known line locks use line on line friction to create the locking effect, and this line on line friction makes it difficult to advance the line lock over suture. Known line locks rely on maintenance of tension in the standing end to prevent the line lock from migrating back along the working end.

In surgical suture applications, the working end is typically trimmed closely to the line lock. As a result, the line lock can easily disassociate from the suture once tension in the standing end is lost. In most, if not all, surgical applications, a free-device floating device such as a line lock can potentially harm adjacent body tissues. Additionally, known line locks are susceptible to loosening during cyclic variations in the tension of the standing end. This cyclic variation in the standing end tension is common in surgical applications as tissues are stressed and then relaxed. Loosening of the line lock thus compromises the securing function for which it was intended.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to line locks that can be used in part to replace surgical knots tied in sutures in open, arthroscopic, and endoscopic procedures. By increasing the size of the line locks, it is also appreciated that the line locks can be used outside of surgical procedures for any use where it is desired to selectively adjust and/or tie off a line such as a rope, cord, string, or other conventional type of line.

Figure 1:
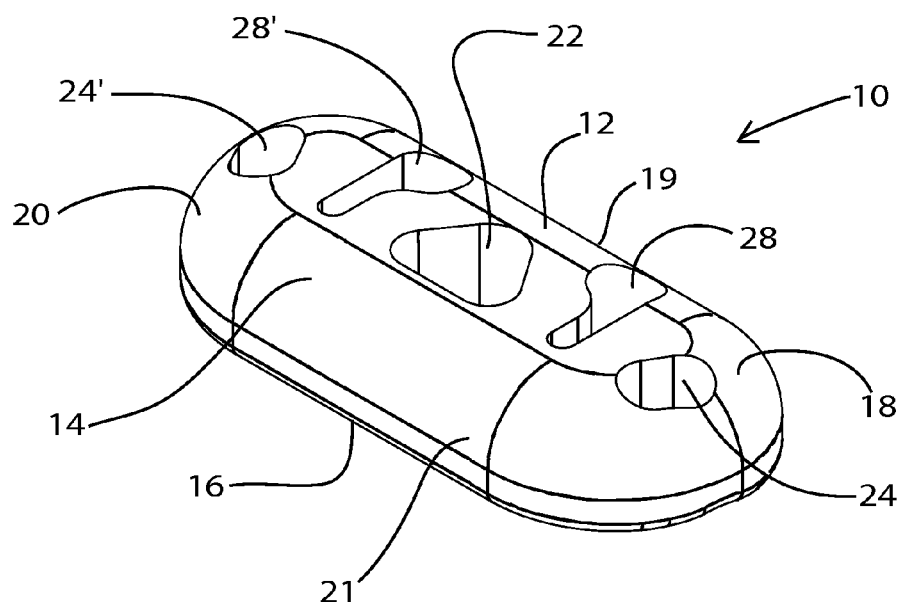
FIG. 1 is a perspective view of an adjustable line lock.

Depicted in FIG. 1 is one embodiment of a line lock 10 incorporating features of the present invention. Line lock 10 comprises an elongated body 12 having a top surface 14 and an opposing bottom surface 16 that each extend between a first end 18 and an opposing second end 20. Body 12 also has a first side 19 and an opposing second side 21 extending between first end 18 and second end 20. In the embodiment depicted, body 12 has a substantially rectangular configuration with rounded ends. As will be apparent from the following disclosure, however, body 12 can be any desired configuration such as triangular, circular, square or any other polygonal or irregular configuration.

In typical surgical applications, body 12 has a maximum dimension D along its length (FIG. 2) which is typically less than about 2 cm, more commonly less than about 1.5 cm, and even more commonly less than about 1 cm. Other dimensions can also be used. By way of example and not by limitation, in one embodiment body 12 has a height in a range between about 1 mm to about 1.5 mm, a width in a range between about 2 mm to about 3 mm, and length D in a range between about 5 mm to about 8 mm. In non-surgical applications, body 12 can be any desired dimension. For example, maximum dimension D can be in a range from about 5 cm to about 0.5 m. Again, other dimensions can also be used.

For use in surgical applications, body 12 can be comprised of any biocompatible material. The biocompatible material can be bioabsorbable or non-bioabsorbable. Examples of typical materials include non-bioabsorbable plastic, bioabsorbable plastic, synthetic tissue, and allograft tissue. In non-surgical applications, body 12 can be made of any desired material such as metal, plastic, wood, fiberglass, composite, or the like.

As depicted in FIG. 1, centrally extending through body 10 between top surface 14 and bottom surface 16 is a primary passageway 22. As used in the specification and appended claims, the term "passageway" is broadly intended to include closed apertures, such as depicted by primary passageway 22, partially bound apertures, open channels, recesses, grooves, slots, and the like, that are capable of receiving a line and at least partially retaining the line therein. The term "line" as used in the specification and appended claims is broadly intended to include suture, cord, rope, filament, wire, cable, and any other form of line.

Extending between surfaces 14 and 16 at first end 18 of body 12 is a first secondary passageway 24. A second secondary passageway 24' extends between surfaces 14 and 16 at second end 20. Extending through body 12 at a location between primary passageway 22 and first secondary passageway 24 is a first working passageway 28. In one embodiment, although not necessarily required, first working passageway 28 is disposed between primary passageway 22 and first secondary passageway 24 such that a geometric line segment 36 (FIG. 2) can be extended between primary passageway 22 and first secondary passageway 24 so that line segment 36 intersects with first working passageway 28. Similar to first working passageway 28, a second working passageway 28' extends through body 12 at a location between primary passageway 22 and second secondary passageway 24'.

Each working passageway 28 and 28' has an elongated transverse cross sectional area that extends between a first end 38 and an opposing second end 40. Each working passageway 28, 28' comprises an enlarged access region 32 at first end 38 which communicates with a constricted capture slot 34 at second end 40. Access region 32 is sized to enable easy feeding of a line into and through the corresponding working passageways 28, 28'. Accordingly, although access region 32 can be slightly smaller than the transverse cross sectional area of the line which is to be passed therethrough, access region 32 typically has a transverse cross sectional area that is equal to or slightly larger than the transverse cross sectional area of the line that is to be passed therethrough.

In contrast, capture slot 34 has a width W that is substantially equal to or less than the diameter of the line that is to be passed through working passageways 28, 28'. For example, in one embodiment width W is less than about 0.9 times the diameter of the line and more commonly less than about 0.75 times the diameter of the line. It is appreciated that working passageways 28, 28' can come in a variety of different configurations. For example, capture slot 34 can come in a variety of different constricted, tapered, or notched shaped configurations that are capable of securely retaining a line through wedged engagement. For line made of less compressible material, such as metal, the required difference between the width W and the diameter of the line may be less than the examples given above.

Figure 2:
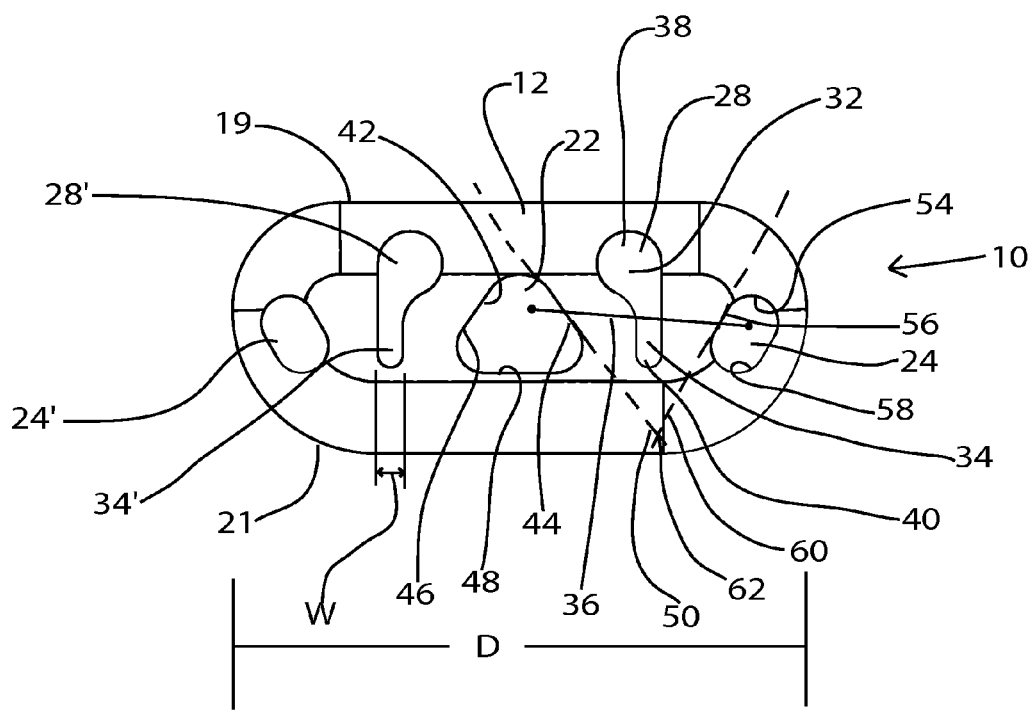
FIG. 2 is a top plan view of line lock shown in FIG. 1.

As depicted in FIG. 2, central passageway 22 is bounded by an interior surface 42 of body 12 having a substantially triangular transverse cross section. Interior surface 42 comprises a first side face 44 disposed toward first working passageway 28, a second side face 46 disposed toward second working passageway 28' and which intersects with first side face 44, and a third side face 48 extending between first side face 44 and second side face 46. Although side faces 44 and 46 are shown as being substantially flat, in alternative embodiments side faces 44 and 46 can be cured or irregular. In one embodiment, however, first side face 44 is substantially disposed in or tangent to a first plane illustrated by dashed line 50. With reference to FIG. 2, plane 50 slopes toward second end 40 of first working passageway 28 as plane 50 extends from first side 19 of body 12 to second side 21.

First secondary passageway 24 is bounded by an interior surface 54 of body 12 having an elongated transverse cross section. Interior surface 54 comprises a first side face 56 disposed toward first working passageway 28 and an opposing second side face 58. Although side faces 56 and 58 are shown as being substantially flat, in alternative embodiments side faces 56 and 58 can also be curved or irregular. Again, in one embodiment first side face 56 is substantially disposed in or tangent to a second plane illustrated by dashed line 60. With reference to FIG. 2, second plane 60 slopes toward second end 40 of first working passageway 28 as second plane 60 extends from first side 19 of body 12 to second side 21.

In the above discussed configuration, first plane 50 and second plane 60 are disposed so as to be converging as they extend from first side 19 of body 12 to second side 21. In the embodiment depicted, planes 50 and 60 intersect at a location 62 on body 12 that is at least substantially aligned with a central longitudinal axis of capture slot 34. In other embodiments, location 62 can be directly adjacent to body 12 or at a distance from body 12. Likewise, location 62 need not be aligned with the central longitudinal axis of capture slot 34. Although not required, in one embodiment planes 50 and 60 are disposed at equally opposing angles relative to the central longitudinal axis of capture slot 34. Furthermore, planes 50 and 60 can intersect so as to form an inside angle therebetween in a range between about 5° to about 85°.

Second secondary passageway 24' has substantially the same configuration as first secondary passageway 24. Likewise, second secondary passageway 24' has substantially the same relative position to second working passageway 28' and second side face 46 of primary passageway 22 as first secondary passageway 26 has to first working passageway 28 and first side face 44 of primary passageway 22. As such, the discussion with regard to planes 50 and 60 are also applicable to primary passageway 22 and second secondary passageway 24'.

By way of example of the passageways and not by limitation, for use with a size USP #2 braided suture, which has a diameter in a range between about 0.5 mm to about 0.6 mm, primary passageway 22 has a length in a range between about 1.3 mm to about 1.5 mm and a width in a range between about 1 mm to about 1.3 mm. Secondary passageways 24 and 24' have a width of about 0.8 mm and a length in a range between 1 mm to about 1.3 mm. Access region 32 of working passageways 28 and 28' have width in a range between about 0.7 mm to 1 mm while capture slots 17 have a width in a range between about 0.3 mm to 0.4 mm.

Figure 3:
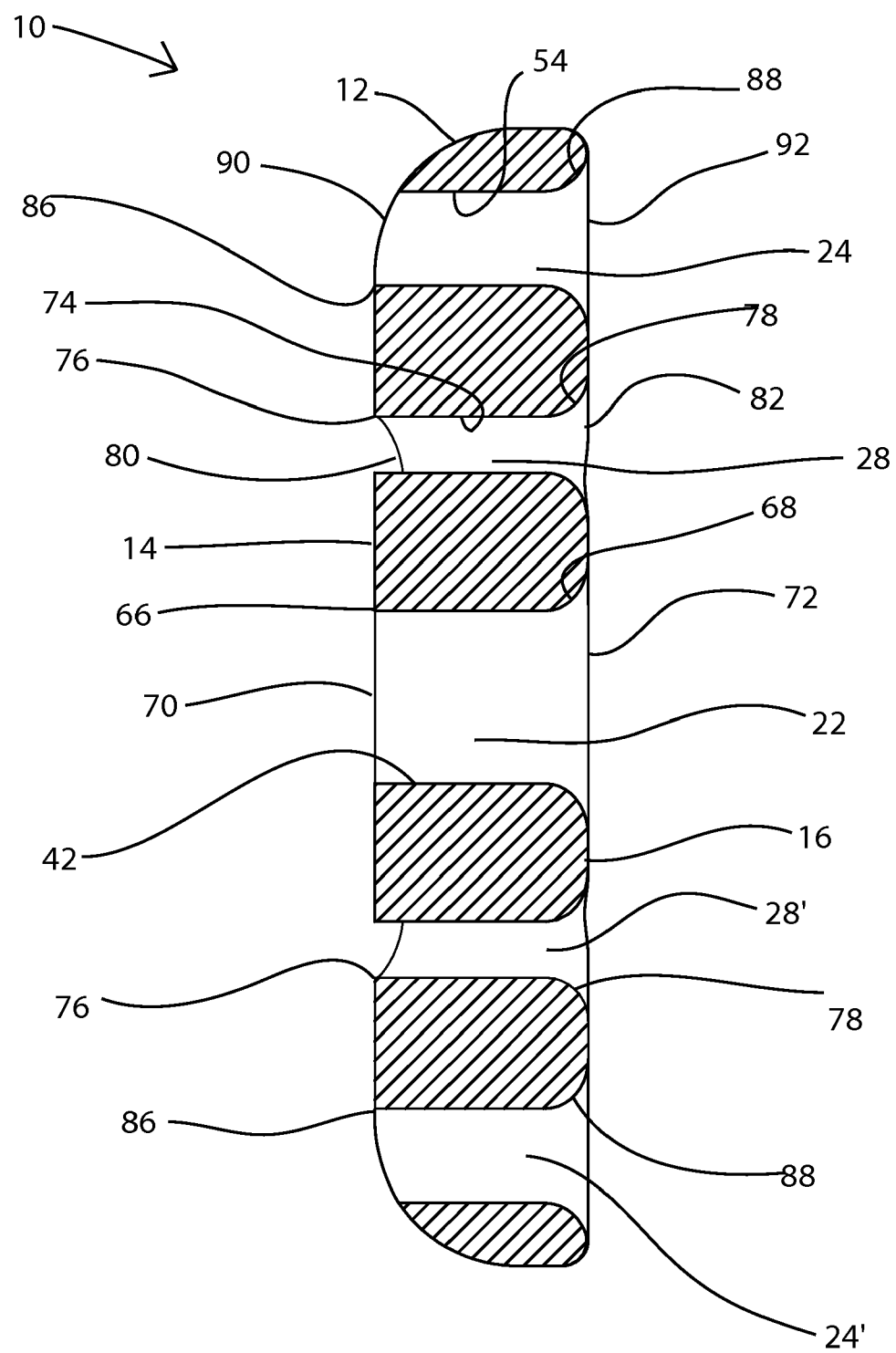
FIG. 3 is an elevated cross sectional side view of the line lock shown in FIG. 1.

Depicted in FIG. 3, interior surface 42 of primary passageway 22 extends to a top outside corner 66 and an opposing bottom outside corner 68. Top outside corner 66 bounds a top primary opening 70 while bottom outside corner 66 bounds a bottom primary opening 72. Similarly, first working passageway 28 has an interior surface 74 that extends to a top outside corner 76 and an opposing bottom outside corner 78. Top outside corner 76 bounds a top working opening 80 while bottom outside corner 76 bounds a bottom working opening 82. Likewise, interior surface 54 of first secondary passageway 24 extends to a top outside corner 86 and an opposing bottom outside corner 88. Top outside corner 86 bounds a top secondary opening 90 while bottom outside corner 86 bounds a bottom secondary opening 92.

For reasons as will be discussed below in greater detail, each of top outside corners 66, 76, and 86 has a radius of curvature that is smaller than the radius of curvature of the corresponding bottom outside corners 68, 78, 88. By way of example and not by limitation, in one embodiment top outside corners 66, 76, and 86 each have a radius of curvature in a range between about 0 mm to about 1 mm with about 0 mm to about 0.5 mm being more common. In contrast, bottom outside corners 68, 78, and 88 each have a radius of curvature in a range between about 0.25 mm to about 2 mm with about 0.5 mm to about 1.5 mm being more common. Other dimensions can also be used, particularly outside of the surgical area. In yet other embodiments it is appreciated that the top outside corners and the bottom outside corners can have the same radius of curvature or that only one or more of the top outside corners may be smaller than one or more of the bottom outside corners. In still other embodiments, it is appreciated that only a portion of one or more of the top outside corners may be smaller than a portion of one or more of the bottom outside corners.

It is again noted that second secondary passageway 24' and second working passageway 28' having substantially the same configuration as first secondary passageway 24 and first working passageway 28, respectively. As such, the same discussion with regard to the outside corners are also applicable thereto. Likewise, like elements are identified by like reference characters.

Figure 4A:
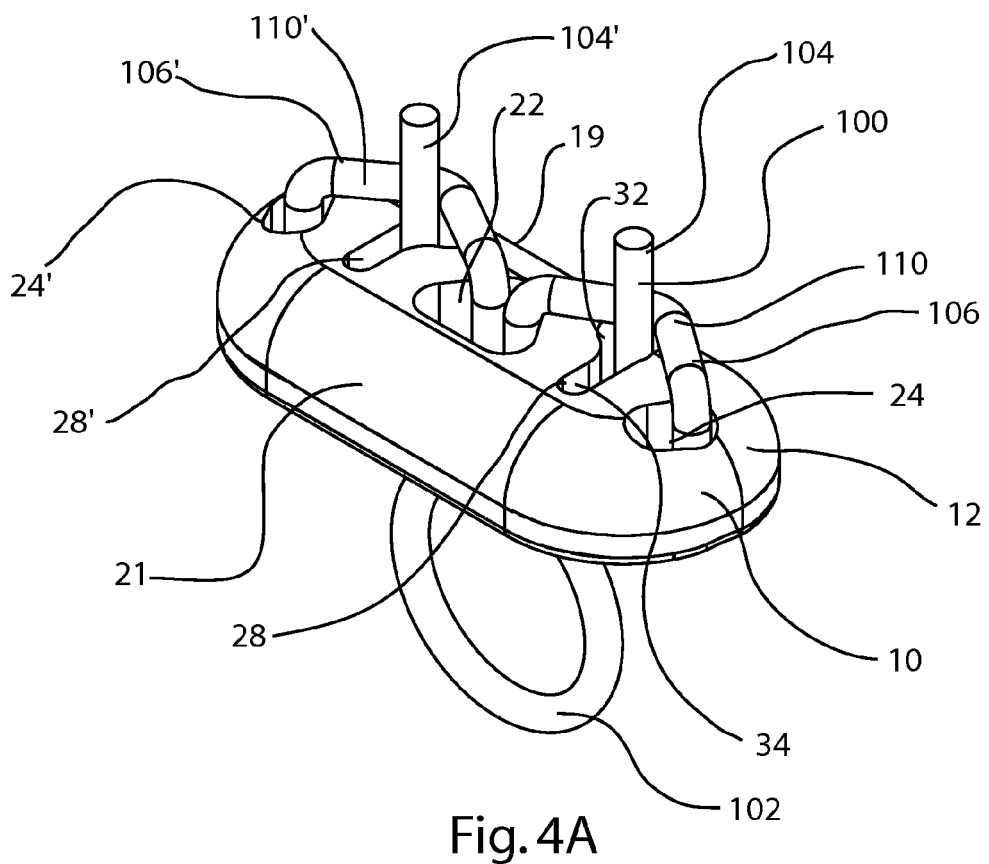
FIG. 4A is a perspective view of the line lock shown in FIG. 1 with a line routed therethrough in a slack unlocked position.

Depicted in FIG. 4A is a line 100 adjustably mounted on line lock 12. Line 100 comprises a standing portion 102 in the form of a loop which extends below primary passageway 22, a first working portion 104 which extends out of first working passageway 28, and a first locking portion 106 extending therebetween. It is appreciated that each of the sections 102, 104, and 106 of line 100 are relative to each other in that they change as line 100 is adjusted on line lock 10. Line 100 further includes a second working portion 104' which extends out of second working passageway 28' and a second locking portion 106' that extends between standing portion 102 and second working portion 104'.

First locking portion 106 extends up through primary passageway 22, down through first secondary passageway 24, and then up through first working passageway 28. The section of locking portion 106 extending between primary passageway 22 and first secondary passageway 24 is referred to as compression section 110. Line 100 passes up through first working passageway 28 so that first working portion 104 is disposed between compression section 110 and capture slot 34. Second locking portion 106' is similarly passed through passageways 22, 24', and 28'.

During use, standing portion 102 of line 100 is typically looped around, embedded within, or passed through tissue, or some other structure. To secure standing portion 102 to the structure, unwanted slack is removed from standing portion 102. This is accomplished by sliding line lock 10 over standing portion 102 and/or pulling on working portion 104 and/or 104' so that the unwanted slack is pulled through line lock 110. In either event, at least one of working portions 104 and 104' increases in length while standing portion 102 shortens.

In the configuration depicted in FIG. 4A, line 100 is passing through enlarged access regions 32 of working passageways 28 and 28'. In this position, relative locking portions 106 and 106' freely slide through corresponding passageways of line lock 10 as the unwanted slack from standing portion 102 is removed. A mild tension force is typically applied to working portions 104 and 104' as the unwanted slack is removed. The applied force pushes compression section 110 and 110' back toward first side 19 of body 12 and thus away from capture slots 34, 34'. In turn, the portion of line 100 passing through primary passageway 22 and secondary passageways 24 and 24' also naturally slides back within the passageways toward first side 19 of body 12. This movement of line 100 helps to decrease frictional resistance on line 100.

Figure 4B:
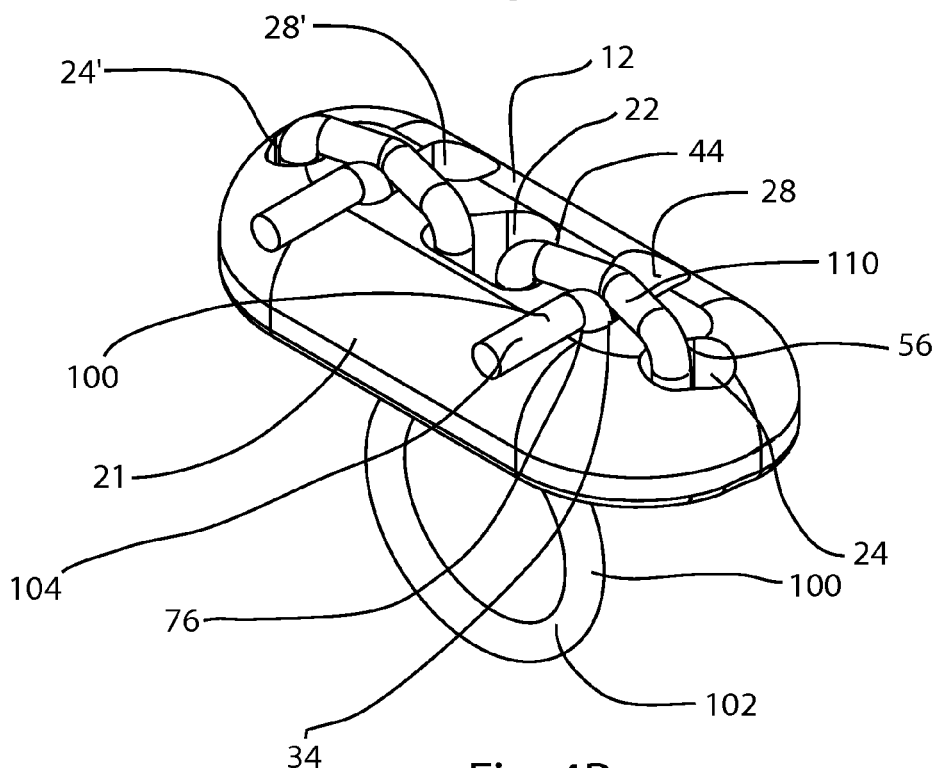
FIG. 4B is a perspective view of the line lock shown in FIG. 4A with the line in a tensioned locked position.

Once the slack is removed from standing portion 102, further force is applied to working portions 104, 104' and/or line lock 10 so as to tension locking portions 106, 106' on line lock 10. As depicted in FIG. 4B, as line 100 is tensioned, the diverging side face 44 of primary passageway 22 and side face 56 of first secondary passageway 24 cause the portions of line 100 passing therethrough, and thus compression portion 110 extending therebetween, to slide toward first side 21 of body 12.

Furthermore, as line 100 is tensioned, compression portions 110, 110' are shortened causing them to move into a more linear orientation. As a result of the above, tensioning of line 100 causes compression portions 110, 110' to force working portions 104, 104' toward corresponding capture slots 34, 34'. In turn, at least a portion of line 100 within working passageways 28 and 28' is forced into corresponding capture slots 34, 34' so that line 100 is secured therein by wedged frictional engagement. That is, line 100 is secured by compression within capture slots 34, 34' because line 100 has a diameter larger than the width of capture slots 34, 34'. Once line 100 is captured under compression in capture slots 34, 34', line 100 will remain captured even if there is a complete loss of tension in standing end 102. Thus, "locking" of line lock 10 to line 100 ensures that line lock 10 will not become separated from line 100, even under cyclic changes in line tension in standing end 102. Furthermore, line lock 10 is continuously adjustable in that further tension can be applied to standing portions 104 and/or 104' at any time to remove additional slack from standing portion 102 while retaining line 100 locked to line lock 10.

The passageways extending through line lock 10 are also configured such that as compression portions 110 and 110' force line 100 into capture slots 34 and 34', compression portions 110 and 110' also fold and/or bias working ends 104 and 104' over and/or against top outside corner 76 of capture slots 34 and 34'. In view of the relatively small radius of curvature of top outside corner 76, the engagement between the captured working ends 104 and 104' and top outside corner 76 creates a high degree of friction which forms a secondary locking mechanism between line 100 and line lock 10. As such, the engagement between capture working ends 104 and 104' and top outside corner 76 prevents backward movement of line lock 10 relative to line 100.

In the embodiment depicted in FIG. 4B, compression portion 110 is disposed above a portion of top outside corner 76 so as to directly bias working ends 104 against top outside corner 76. Compression portion 110 is also shown disposed directly above a portion of working end 104 that is biasing against top outside corner 76. In alternative embodiments, compression portion 110 when tensioned can extend between central passageway 22 and secondary passageways 24 without passing over working passageway 28. That is, compression portion 110 can pass at a location toward second side 21 of line lock 10 that is spaced apart from working passageway 28. In this embodiment, compression portion 110 still passes over working end 104, thereby remotely causing working end 104 to fold over and bias against top outside corner 76.

One of the unique features of the present embodiment is that as line lock 10 is advanced toward standing end 102 when standing end 102 is not under tension, i.e., when slack is being removed from standing end 102, working ends 104 and 104' tend to push away compression portions 110 and 110', as discussed above, thereby minimizing frictional engagement between working ends 104, 104', compression portions 110, 110' and line lock 10. As a result, line lock 10 can be easily advanced on line 100.

Furthermore, unlike some other continuously adjustable line locks known in the art that use a loop portion to draw in and wedge a portion of a line within a bore hole, compression portions 110 and 110' traverse a substantially straight path because they are constrained by secondary passageways 24 and 24' and primary passageway 22. This substantially straight path translates to a lower frictional resistance to sliding not possible with other adjustable line locks known in the art.

As previously discussed, line 100 is routed through passageways 22, 24, and 28 so as to pass over the outside corners of the passageways. When a tensioned section of line 100 passes around a first outside corner of line lock 10, friction produced between line 100 and the corresponding outside corner cause a decrease in tension on the portion of line 100 extending away from the outside corner on the side opposite the tensioned section. The friction produced at the outside corner must be overcome in order to cause line 100 to slide. Similarly, as the line passes around subsequent outside corners away from the tensioned section, each subsequent corner produces an incremental decrease in line tension and a corresponding incremental increase in friction that must be overcome to cause line 100 to slide. The loss in tension and increase in friction diminishes for each subsequent corner. Thus, the first corners are the most significant.

Figure 6:
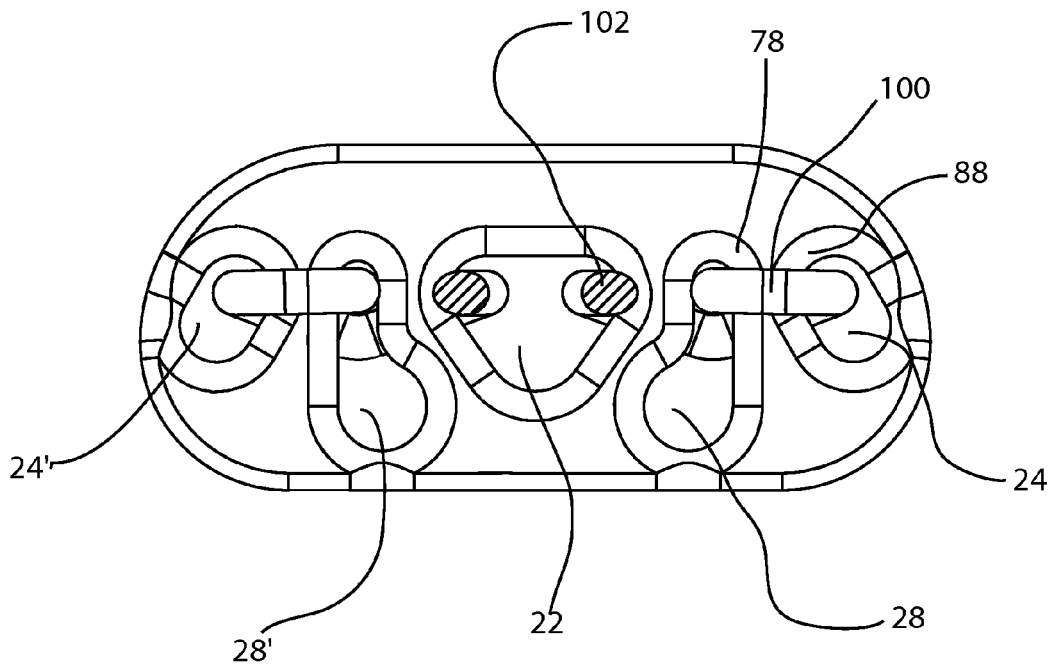
FIG. 6 is a bottom plan view of the line lock shown in FIG. 4B.

As depicted in FIG. 6, in view of the above discussion, when working end 104 is tensioned and standing end 102 is slack, line 100 extending from working end 104 toward line lock 10 first turns on bottom outside corner 78 of working passageway 28 and bottom outside corner 88 of secondary passageway 24. As a result of the fact that these are the closest outside corners to tensioned working end 104, outside corners 78 and 88 will produce the highest frictional resistance. Accordingly, to minimize the frictional resistance produced by outside corners 78 and 88 and thereby ease the sliding of line lock 10 toward standing end 102, outside corners 78 and 88 are generously rounded as previously discussed.

Figure 5:
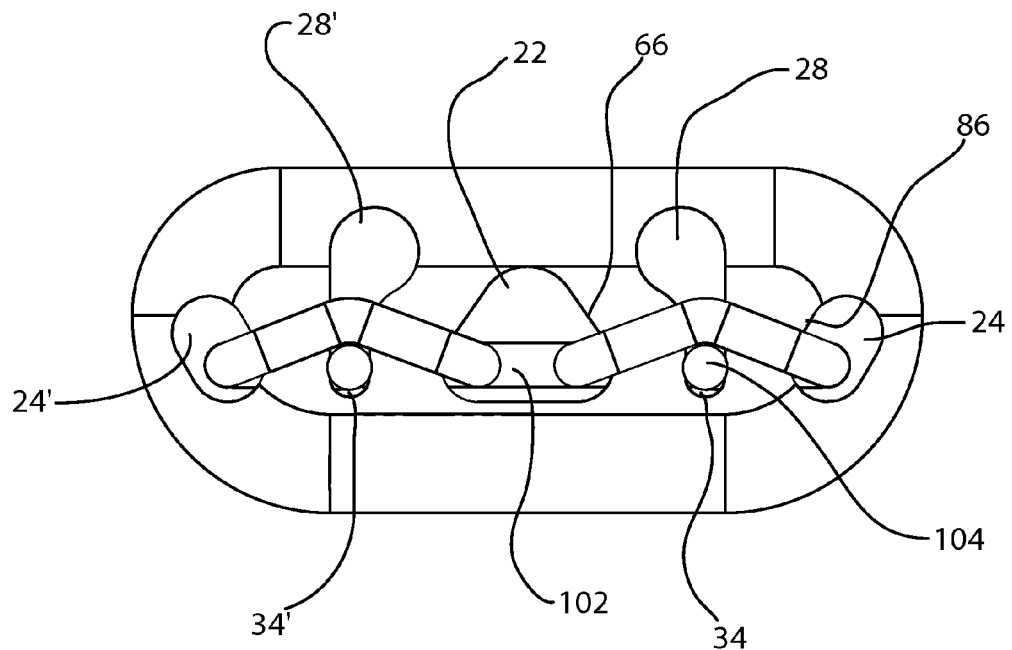
FIG. 5 is a top plan view of the line lock shown in FIG. 4B.

In contrast, as depicted in FIG. 5, when standing end 102 is tensioned and working end 104 is slack, line 100 extending from standing end 102 toward line lock 10 first turns on top outside corner 66 of primary passageway 22 and top outside corner 86 of secondary passageway 24. In view of the fact that these are the closest outside corners to tensioned standing end 102, outside corners 66 and 86 will produce the highest frictional resistance. Accordingly, to maximize the frictional resistance produced by outside corners 66 and 86 and thereby minimizing slipping of line 100 once tensioned, outside corners 66 and 86 are formed relative sharp as previously discussed. More specifically, top outside corners 66 and 86 have a smaller radius of curvature than bottom outside corners 78 and 88. It is noted that not all of each outside corner that bounds a corresponding opening has to have the same radius of curvature. For example, the portion of each outside corner that directly engages line 100 can have a radius of curvature that is different from the remainder of the corresponding outside corner.

Figure 7:
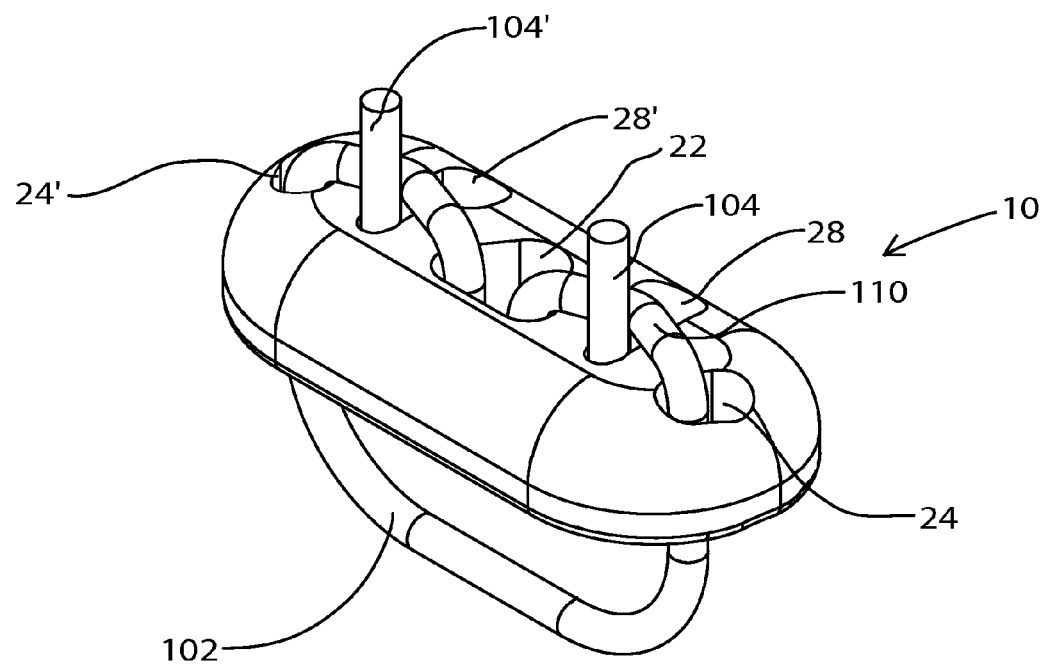
FIG. 7 is a perspective view of the line lock shown in FIG. 4A with the line routed in a different path.

Depicted in FIG. 7, line lock 10 is shown having an alternative routing of line 100. To achieve this routing, working ends 104 and 104' are passed up through secondary passageways 24 and 24', respectively, down through primary passageway 22, and then back up through working passageways 28 and 28', respectively. Again compression portions 110 and 110' are formed that selectively force working ends 104 and 104' toward capture slots 34 as discussed above. In yet another alternative, it is appreciated that one end of line 100 can be routed as shown in FIG. 4A while the opposing end of line 100 is routed as shown in FIG. 7.

Figure 8:
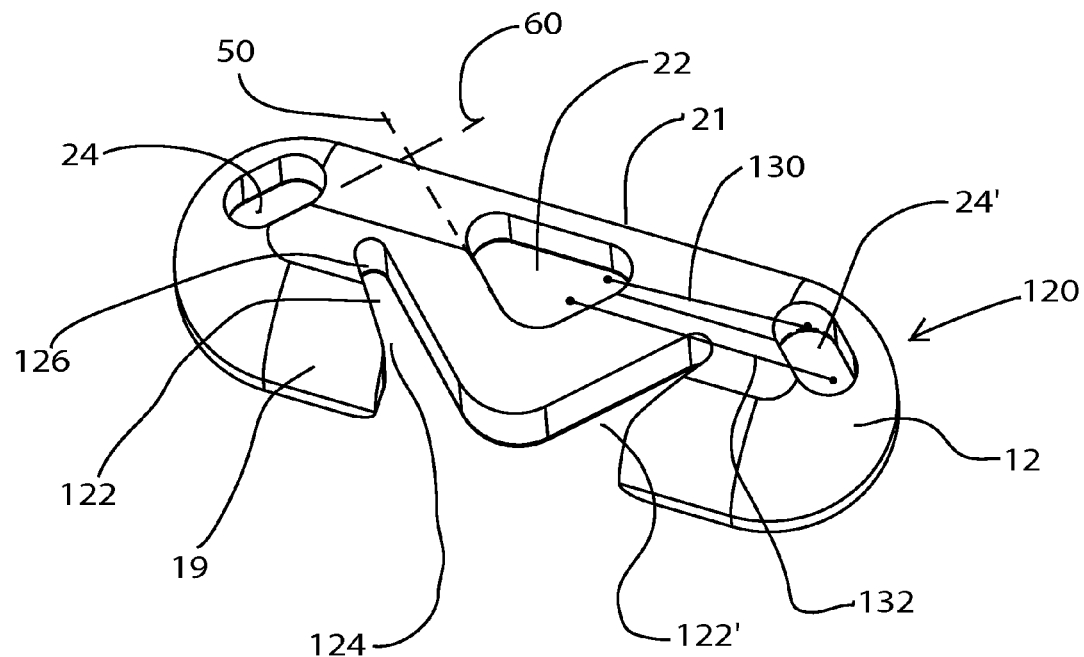
FIG. 8 is a perspective view of an alternative embodiment of the line lock shown in FIG. 1 with open working passageways.

Depicted in FIG. 8 is an alternative embodiment of a line lock 120. It is noted that all common elements of alternative embodiments of line locks disclosed herein are identified by like reference characters. Line lock 120 comprises body 12 having primary passageway 22 and secondary passageways 24 and 24' extending therethrough as discussed above with regard to FIG. 1. In contrast to the circumferentially closed working passageways 28, 28', however, line lock 120 comprises working passageways 122 and 122' that are circumferentially open. That is, each working passageway 122 and 122' comprises an elongated tapered slot having a first end 124 and an opposing second end 126. First end 124 is open along first side 19 of body 12 to facilitate convenient loading of line 100 therein. First end 124 also typically has a width greater than the diameter of line 100 Second end 126 extends to a location between primary passageway 22 and a corresponding one of secondary passageway 24, 24'.

In this embodiment it is noted that the passageways are positioned such that a geometric line segment 130 can be extended between primary passageway 22 and secondary passageway 24' such that line segment 130 does not intersect with working passageway 122'. However, a geometric line segment 132 can also be extended between primary passageway 22 and secondary passageway 24' such that line segment 132 intersects with working passageway 122'. Second end 126 of each working passageway 122, 122' typically has a width substantially equal to or smaller than the diameter of line 100.

Figure 9:
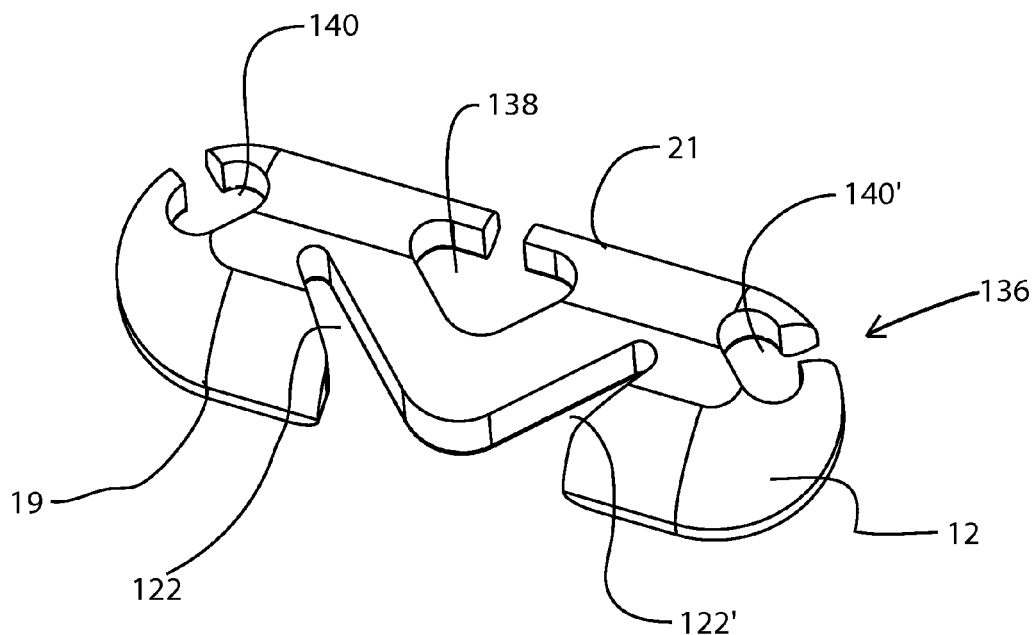
FIG. 9 is a perspective view of another alternative embodiment of the line lock shown in FIG. 1 with open passageways.

Depicted in FIG. 9 is another alternative embodiment of a line lock 136 having substantially the same configuration as line lock 120. In contrast to the circumferentially bounded primary passageway 22 and secondary passageways 24 and 24' of line lock 120 in FIG. 8, however, line lock 136 comprises a partially bounded primary passageway 138 which is open at second side 21 of body 12 and partially bounded secondary passageways 140 and 140' that are also each open at or adjacent to second side 21 of body 12.

Figure 10:
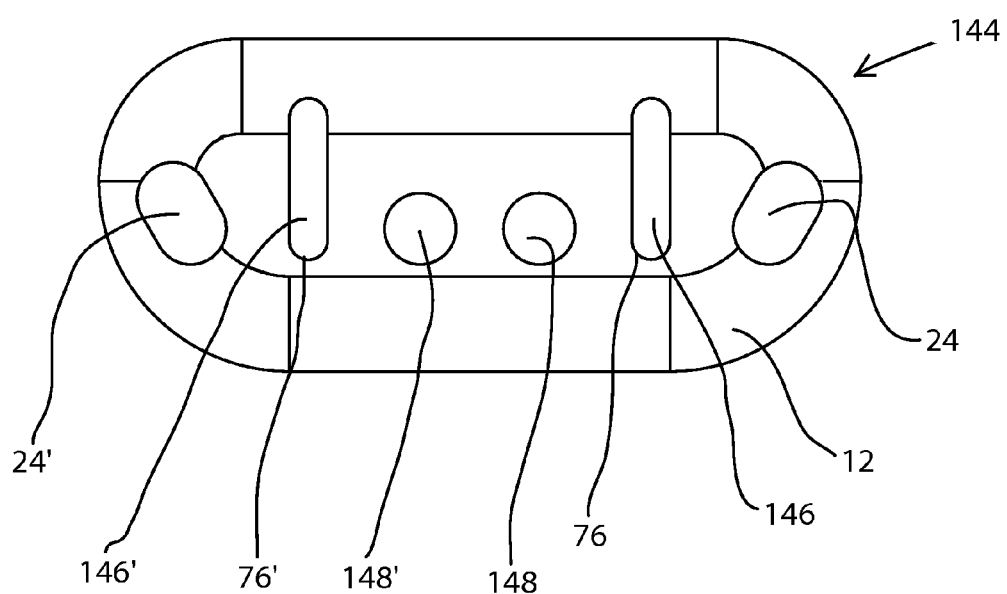
FIG. 10 is a perspective view of another alternative embodiment of the line lock shown in FIG. 1 with dual primary passageways and uniform working passageways.

Two separate locking features were previously discussed with regard to securing line 100 to line lock 10. Specifically, line 100 is secured by being wedged into capture slots 34 and 34' and by biasing working portions 104 and 104' against the top outside corner 76 of each working passageway 28, 28'. In alternative embodiments, it is appreciated that the locking features can be used independently. For example, depicted in FIG. 10 is a line lock 144 having body 12 with secondary passageways 24 and 24'. In contrast to line lock 10, however, line lock 144 comprises working passageways 146 and 146' wherein capture slots 34 have been eliminated. Working passageways 146 and 146' merely comprise elongated channels having a width substantially the same size or larger than the diameter of the line 100 to be passed therethrough. Line 100 is thus primarily secured to line lock 144 as a result of compression portions 110, 110' biasing line 100 against top outside corner 76 of each working passageways 146 and 146' as previously discussed.

Line lock 144 is also distinguished over line lock 10 in that primary passageway 22 has been replaced with a first primary passageway 148 and a spaced apart second primary passageway 148'. Primary passageways 148 and 148' operate with opposing ends of line 100. It is also noted that in alternative embodiments primary passageway(s) and/or the secondary passageways need not be elongated to allow the line passing therethrough to slide toward opposing sides 19 and 21 of body 12 as previously discussed with regard to line lock 10.

Figure 11:
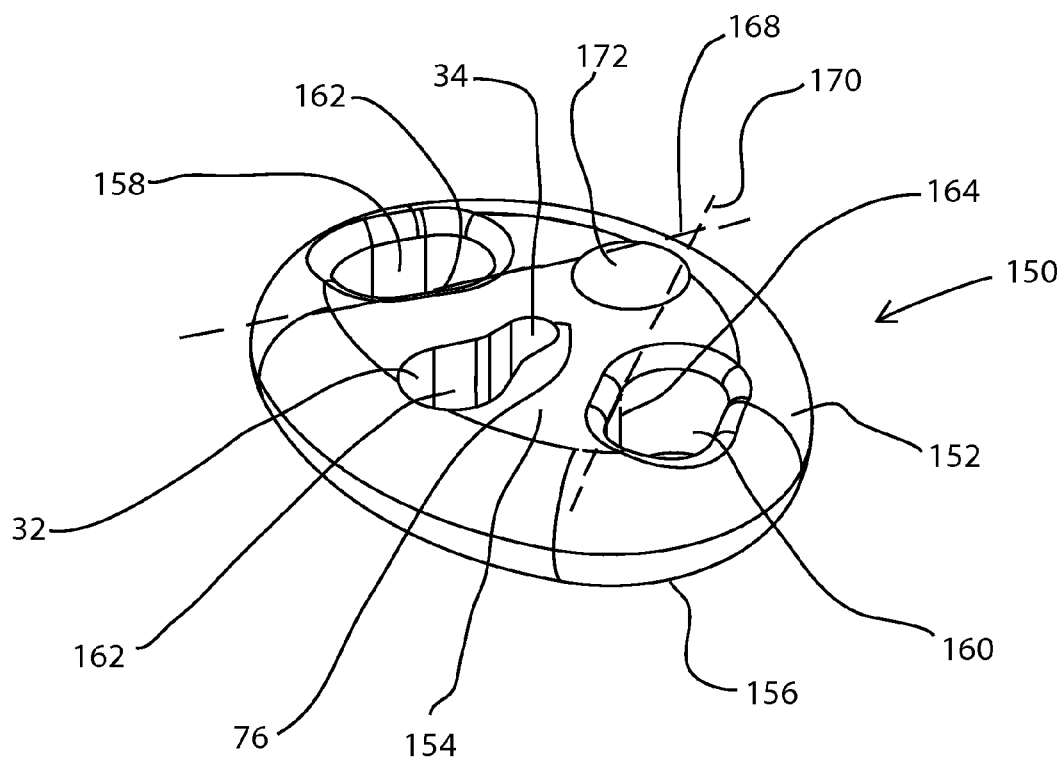
FIG. 11 is a perspective view of a line lock for use with a single strand of line.

Depicted in FIG. 11 is an alternative embodiment of a line lock 150 that is designed to slide along a single strand of line 100. Line lock 150 comprises a substantially disk shaped body 152 having a top surface 154 and an opposing bottom surface 156. Extending through body 152 between surfaces 154 and 156 is a primary passageway 158 and a spaced apart secondary passageway 160. Disposed between passageways 158 and 160 is a working passageway 162. Similar to line lock 10, working passageway 162 of line lock 150 has a first end with enlarged access region 32 and an opposing second end with constricted capture slot 34 thereat.

Primary passageway 158 and secondary passageway 160 have substantially the same elongated circular configuration which is similar to previously discussed secondary passageway 24. Each of passageways 158 and 160 has an inside face 162 and 164, respectively, that is disposed toward working passageway 162. Each inside face 162 and 164 is substantially disposed in or is tangent to a corresponding plane 168 and 170, respectively. Planes 168 and 170 converge toward capture slot 34 of working passageway 162 and diverge away from access region 32.

Also extending through body 152 between top surface 154 and bottom surface 156 is an end passageway 172. Although end passageway 172 can be positioned at a variety of different locations, end passageway 172 is shown aligned with working passageway 162 such that a plane extending between working passageway 162 and end passageway 172 separates primary passageway 158 from secondary passageway 160.

Figure 12A:
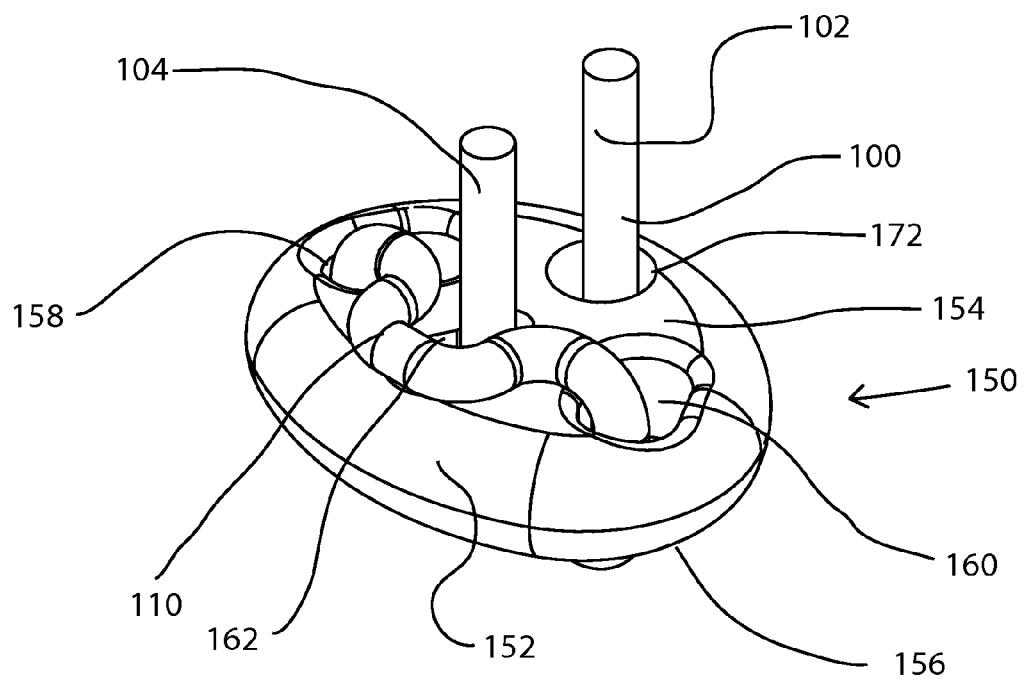
FIG. 12A is a perspective view of the line lock shown in FIG. 11 with a line routed therethrough.
Figure 12B:
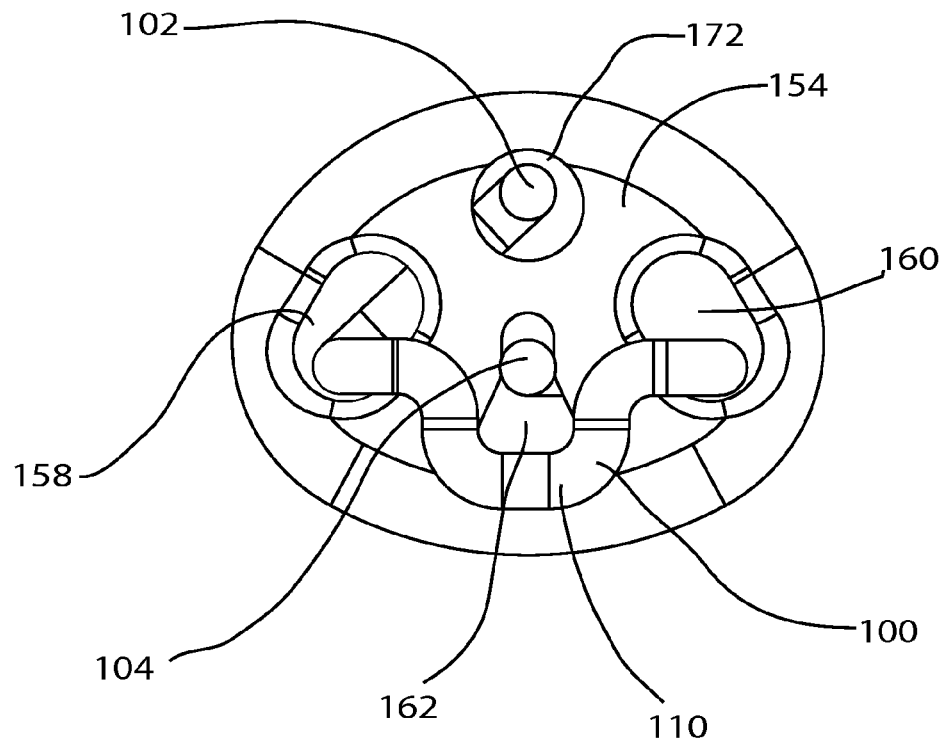
FIG. 12B is a top plan view of the line lock shown in FIG. 12A.
Figure 12C:
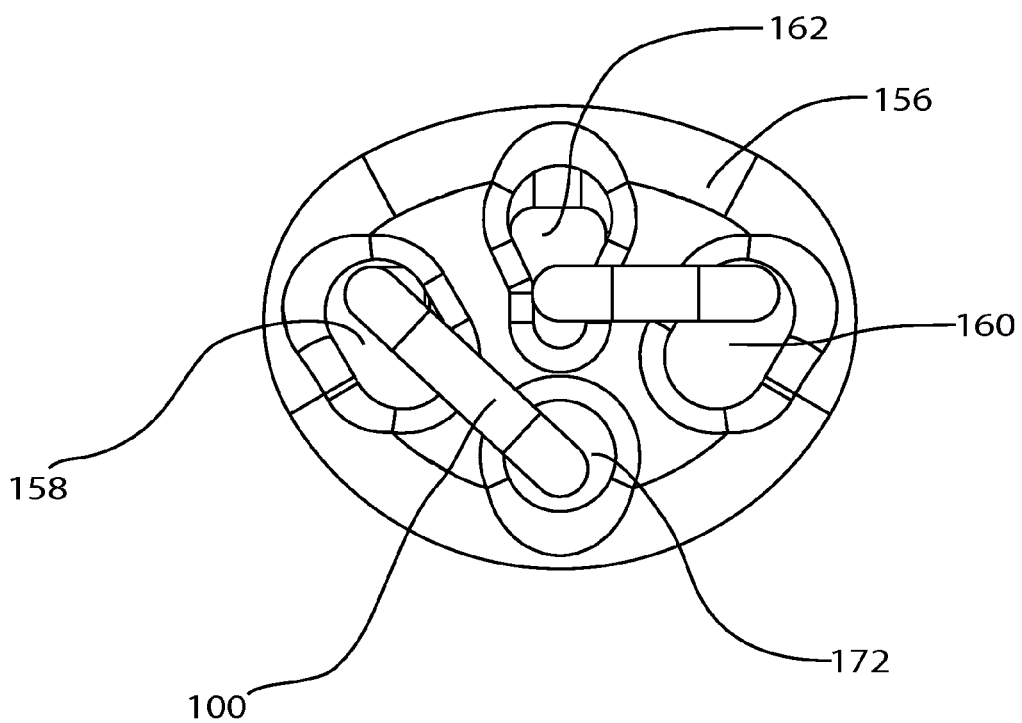
FIG. 12C is a bottom plan view of the line lock shown in FIG. 12A.

During use, as depicted in FIGS. 12A–12C, line 100 is routed through line lock 150 by passing working portion 104 from top surface 154 to bottom surface 156 through end passageway 172, up through primary passageway 158, down through secondary passageway 160, and finally up through working passageway 162. Compression portion 110 of line 100 extends between primary passageway 158 and secondary passageway 160 and is positioned to act upon working portion 104. Line lock 150 can be selectively advanced by pulling working portion 104 away from top surface 154 so that line 100 travels through line lock 150. Alternatively, line lock 150 can be manually slid toward standing portion 102. In either event, the length of standing portion 102 is decreased.

As line 100 is tensioned on line lock 150, line 100 locks on line lock 150 in substantially the same manner that line 100 locks with working passageway 28 as previously discussed with regard to line lock 10. That is, compression portion 110 forces working end 104 toward capture slot 34 so that the portion of line 100 within working passageway 162 is captured by wedged frictional engagement within capture slot 34. Furthermore, compression portion 110 either directly or indirectly biases working portion 104 against the top outside corner 76 of working passageway 162 at the second end thereof so as to increase the frictional engagement between line 100 and line lock 150. Line lock 150 thus provides a continuously adjustable line lock or a one way sliding stop. In alternative embodiments, it is appreciated that line lock 150 can be modified in at least the same ways as discussed with the other line locks disclosed herein.

The embodiment shown in FIGS. 12A–12C is advantageous in certain applications where line lock 150 is positioned behind a first object and working portion 104 and standing portion 102 pass through the first object. In this situation, standing portion 102 is fixed to a second object. By pulling on working portion 104, the first object is drawn irreversibly toward the second object. This is an advantage with surgical sutures where standing end 102 of a suture is attached to normal tissues and line lock 150 is placed behind tissue that has torn away. Standing portion 102 and working portion 104 pass through the torn tissue toward the normal tissue. By pulling on working portion 104 of suture, the torn tissue is pulled into apposition with the normal tissues and line lock 150 maintains the torn tissue adjacent to the normal tissue to facilitate healing of the tissue.

Figure 13A:
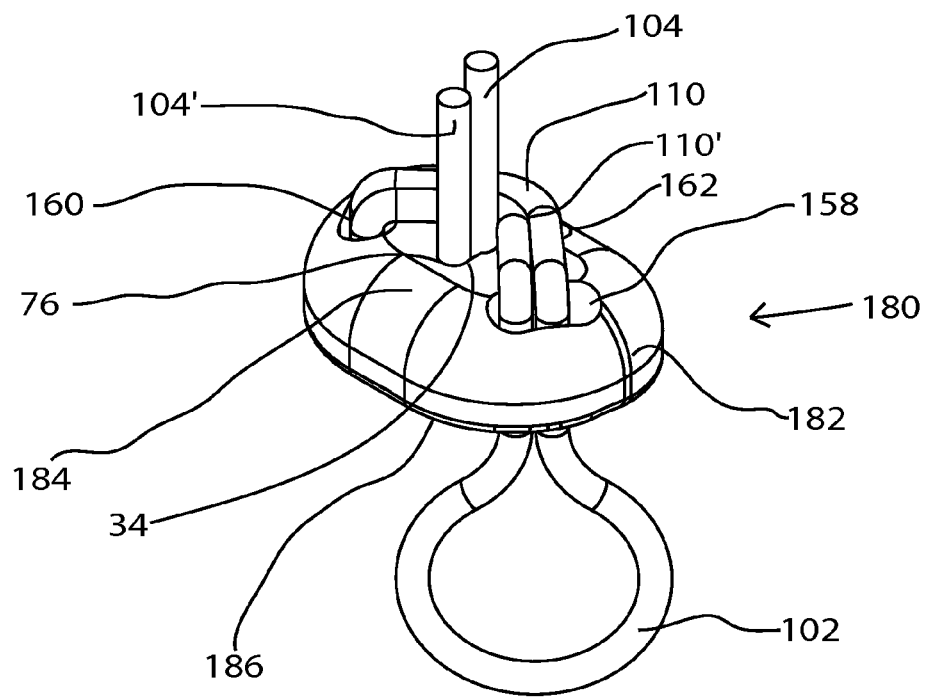
FIG. 13A is a top perspective view of a line lock having dual strands of line routed therethrough.
Figure 13B:
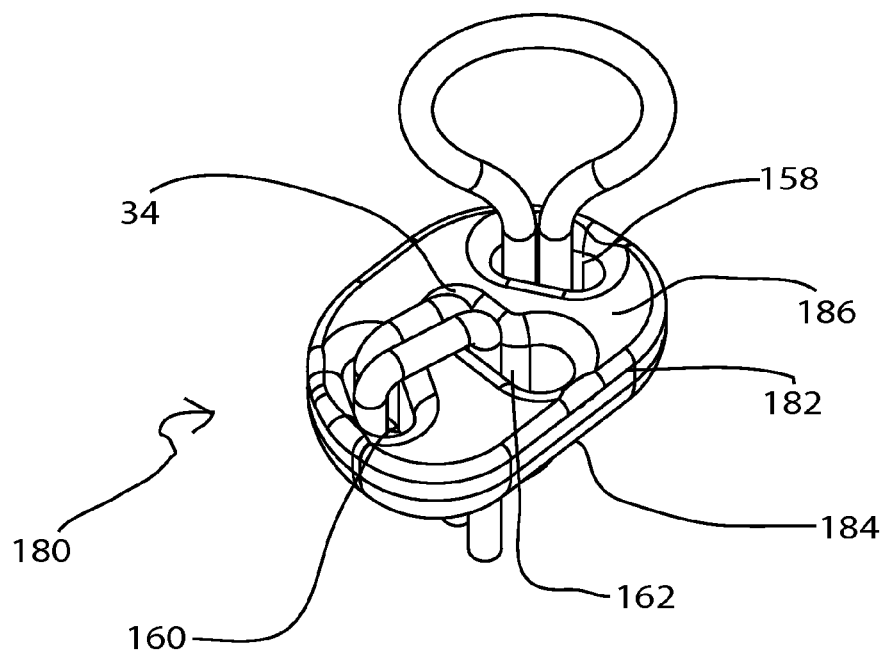
FIG. 13B is a bottom perspective view of the line lock shown in FIG. 13A.

Depicted in FIGS. 13A and 13B is another embodiment of a line lock 180 incorporating features of the present invention. Line lock 180 also comprises a substantially disk shaped body 182 having a top surface 184 and an opposing bottom surface 186. As with line lock 150, line lock 180 includes primary passageway 158, secondary passageway 160, and working passageway 162. Again, although not required, working passageway 162 is disposed such that a geometric line segment can be extended between primary passageway 158 and secondary passageway 160 so that the line segment intersects with working passageway 162. In contrast to line lock 150, line lock 180 does not include end passageway 172.

Each of passageways 158, 160, and 162 is configured to receive a double strand of line 100. Specifically, during use both working end 104 and 104' are passed up through primary passageway 158, down through secondary passageway 160 and then back up through working passageway 162. As a result, standing portion 102 is again formed in a loop that can be looped around, passed through, or otherwise secured to tissue or other structure. Unwanted slack is removed from standing portion 102 by again sliding line lock 180 on line 100 toward standing portion 102 and/or by pulling on one or both of working portions 104 and 104' so that line 100 passes through line lock 180.

When line 100 is tensioned on line lock 180, compression portions 110 and 110' force working portions 104, 104' toward capture slot 34 so that a portion of each line section passing through working passageway 162 is captured by wedged frictional engagement within capture slot 34. Compression portions 110 and 110' also bias working portions 104 and 104' toward and/or against top outsider corner 76 of working passageway 162 so as to increase the frictional engagement between line 100 and line lock 180. As previously discussed with passageways 22, 24, and 28 of line lock 10 in FIGS. 1–6, the radius of curvature of the top outside corner and bottom outside corner of each passageway 158, 160, and 162 can be set so as to further control the ability of line 100 to slide or not slide through the passageway. Other alternatives as discussed with the line locks herein are also applicable to line lock 180. In particular each of the passageways 158, 160, and 162 can also be configured to receive a single strand of line 100. In this configuration the single strand of line 100 is routed in a manner as described above for the double strand of line 100. Instead of the standing portion 102 forming a loop when a double strand of line 100 is used, in this case the standing portion 102 consists of a free end which can be attached to tissue or other structures.

Figure 14A:
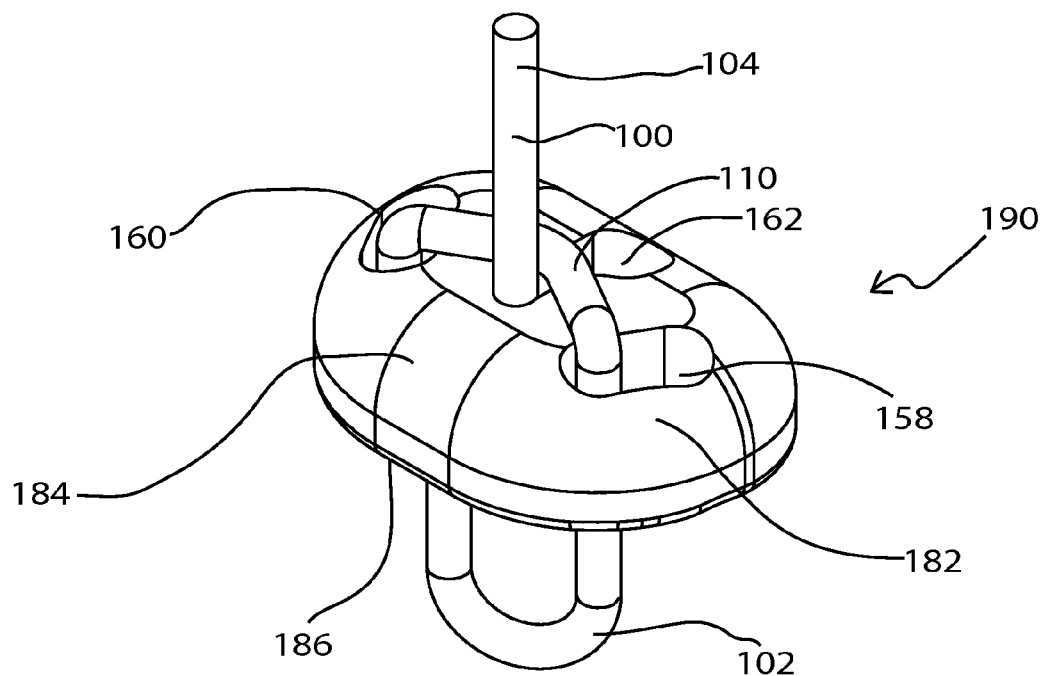
FIG. 14A is a top perspective view of a line lock having a line secured thereto.
Figure 14B:
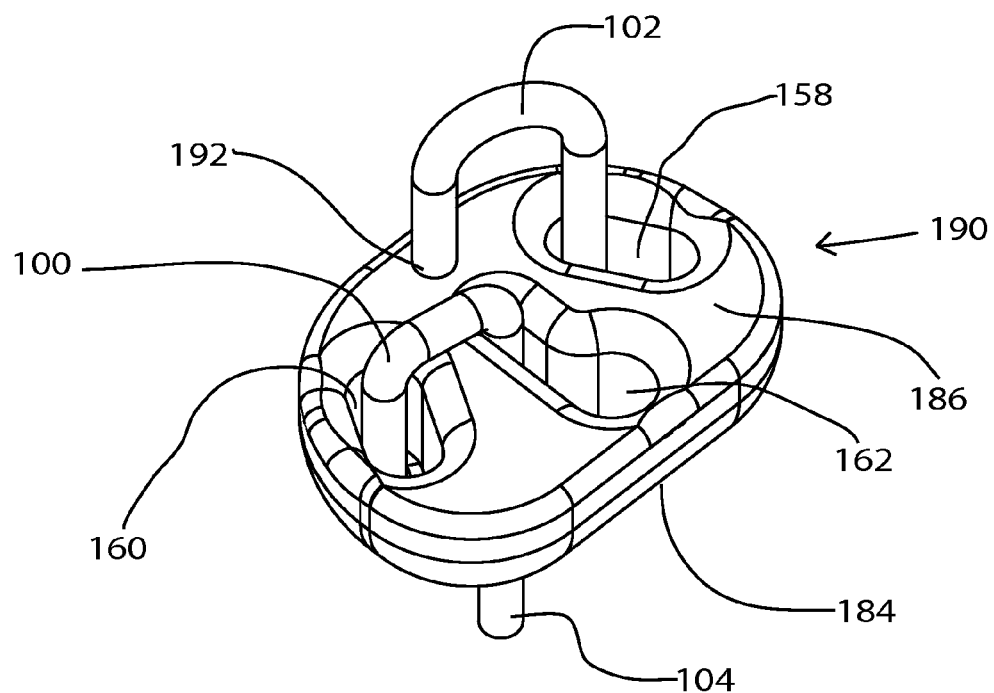
FIG. 14B is a bottom perspective view of the line lock shown in FIG. 14A.

Depicted in FIGS. 14A and 14B is still another embodiment of a line lock 190 incorporating features of the present invention. Line lock 190 has substantially the same configuration as line lock 180 with like elements being referenced with like reference characters. The primary distinction between line locks 180 and 190 is that in line lock 190, an end 192 of line 100 adjacent to standing portion 102 is secured to bottom surface 186 of body 182. End 192 can be secured to body 182 by being integrally molded into body 182 or can be otherwise secured such as by welding or mechanical attachment.

Line lock 190 is also distinguished from line lock 180 in that passageways 158, 160, and 162 need only be configured to receive a single strand of line 100. That is, working end 104 passes up through primary passageway 158, down through secondary passageway 160, and then back up through working passageway 162. Standing portion 102 is again substantially formed into a loop extending from end 192 of line 100 to primary passageway 158. Because end 192 of line 100 is secured to body 182, unwanted slack can be removed from standing portion 102 by pulling line 100 through line lock 190 and/or sliding line lock 190 down line 100. Line 100 is locked to line lock 190 in substantially the same manner as discussed above with regard to the other line locks when line 100 is tensioned on line lock 190.

Figure 15:
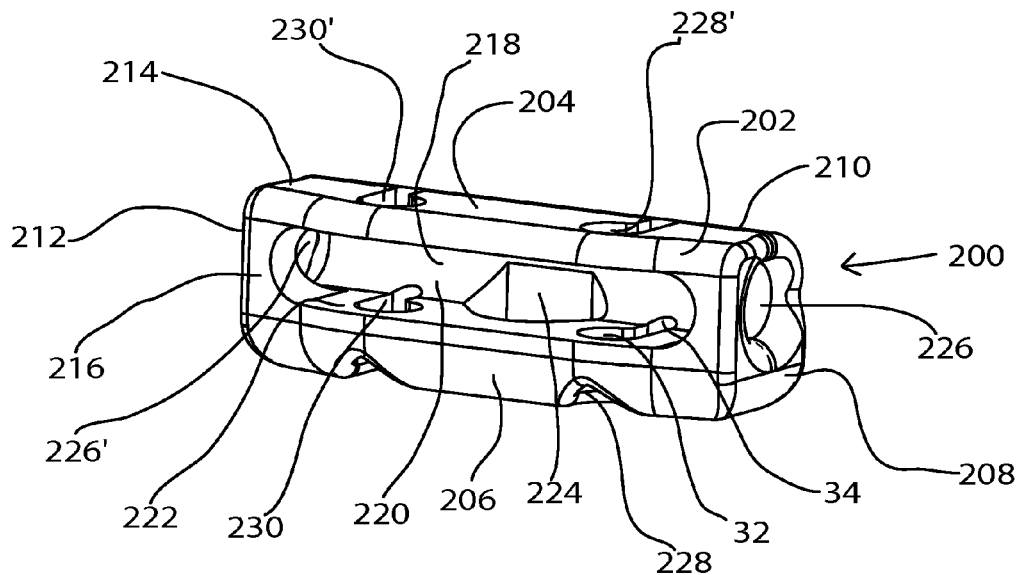
FIG. 15 is a perspective view of an alternative embodiment of a line lock.

Depicted in FIG. 15 is still another embodiment of a line lock 200 incorporating features of the present invention. Line lock 200 comprises an elongated substantially box shaped body 202 comprising a top wall 204 and an opposing bottom wall 206 each extending between a first side wall 208 and a first end 210 and an opposing second side wall 212 and an opposing second end 214. Also extending between top wall 204 and bottom wall 206 is a front wall 216 and an opposing back wall 218.

Partially bounded within body 202 is a hollow chamber 220. An access channel 222 is formed on front wall 216 so as to communicate with chamber 220. Also communicating with chamber 220 is a primary passageway 224. Primary passageway centrally extends through bottom wall 206 to chamber 220. A first secondary passageway 226 extends through first side wall 208 so as to communicate with chamber 220 while a second secondary passageway 226' extends through second side wall 212 so as to communicate with chamber 220. A pair of first working passageways 228 and 228' extend through bottom wall 206 and top wall 204, respectively, in vertical alignment between primary passageway 224 and first secondary passageway 226.

Similarly, a pair of second working passageways 230 and 230' extend through bottom wall 206 and top wall 204 in vertical alignment between primary passageway 224 and second secondary passageway 226'. As with the prior working passageways, each of working passageways 228, 228' and 230, 230' has a first end towards front wall 226 with an enlarged axis region 32 and an opposing second end toward back wall 218 with a capture slot 34 formed thereat.

Figure 16A:
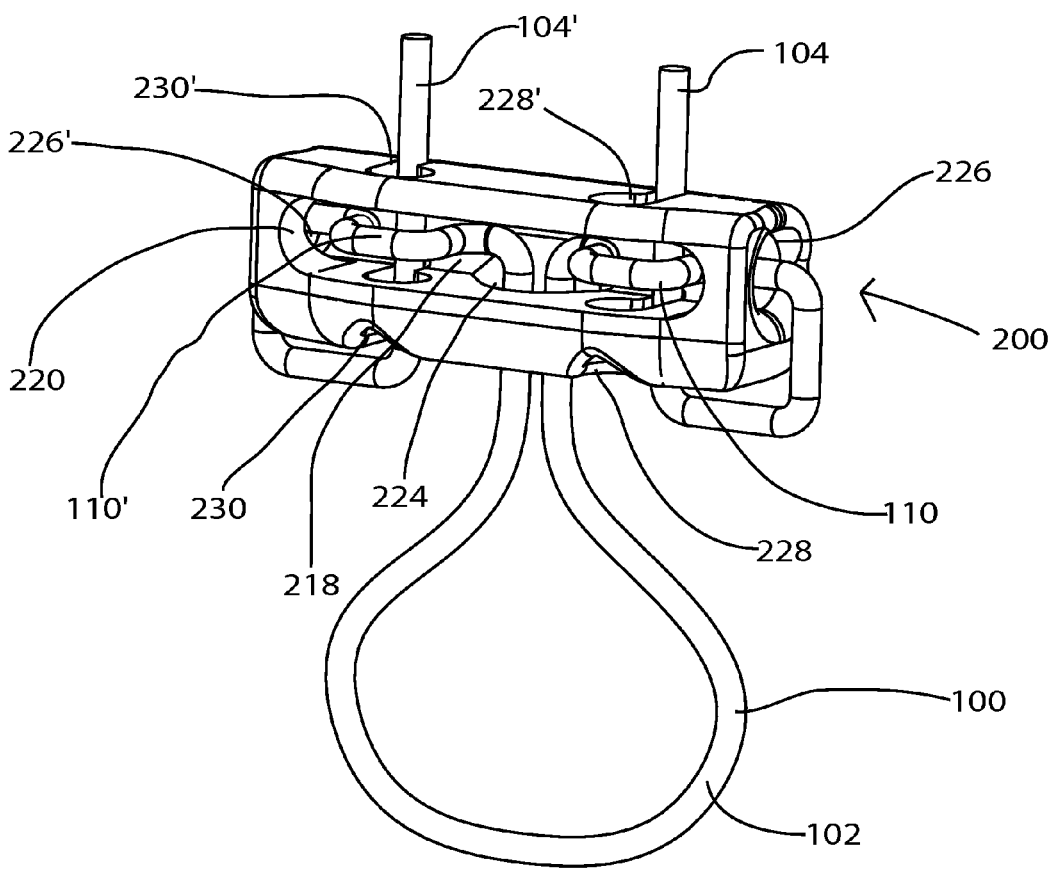
FIG. 16A is a perspective view of the line lock shown in FIG. 15 with a line routed therethrough.
Figure 16B:
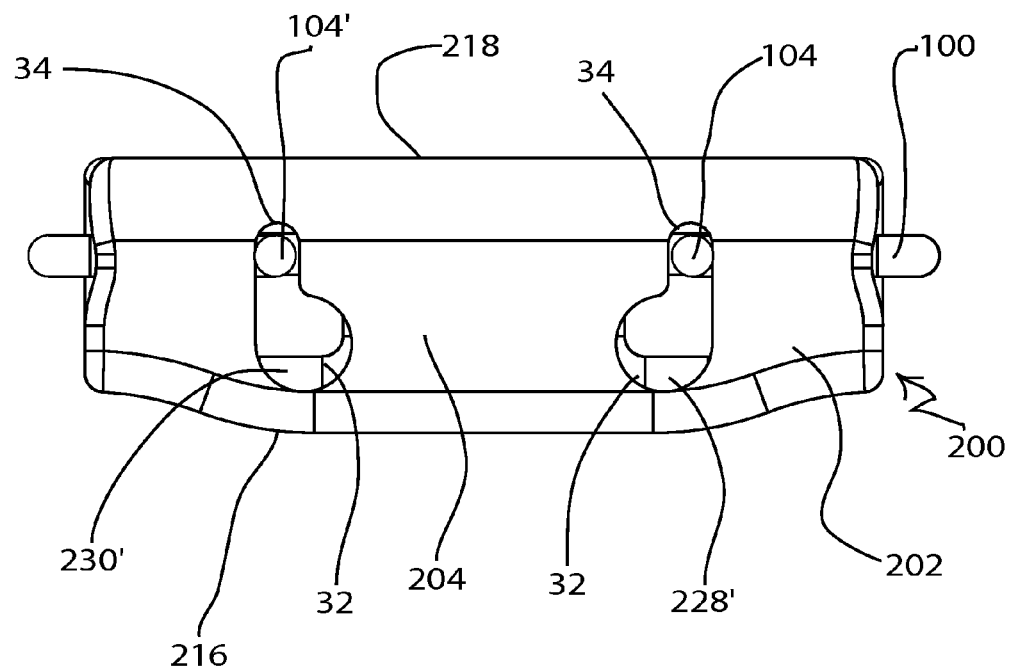
FIG. 16B is a top plan view of the line lock shown in FIG. 16A.
Figure 16C:
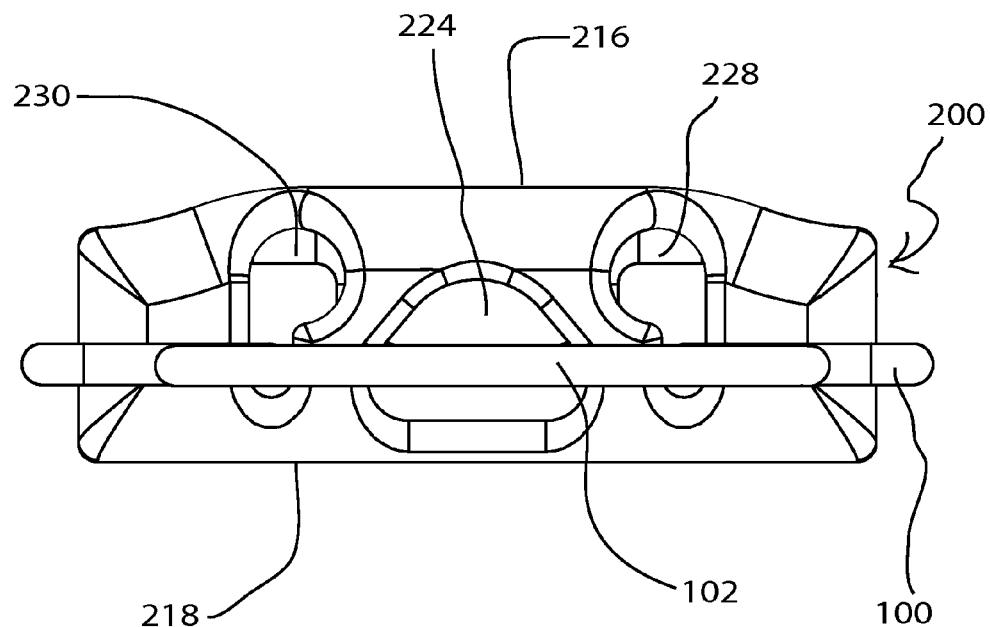
FIG. 16C is a bottom plan view of the line lock shown in FIG. 16A.

During use, as depicted in FIG. 16A-16C, working portions 104 of line 100 are passed up through primary passageway 224 into chamber 220. Working portion 104 then passes out of chamber 220 through first secondary passageway 226. Finally, working portion 104 passes up through first working passageway 228, through chamber 220, and then out through first working passageway 228'. Compression portion 110 of line 100 extends from primary passageway 224 to first secondary passageway 226. Working portion 104 is routed such that line 100 passes between compression portion 110 and back wall 218.

In like manner, working portion 104' extends from chamber 220 out through second secondary passageway 226'. Working portion 104' then extends up through second working passageway 230, through chamber 220, and then out through second working passageway 230'. Again, line 100 extends between compression portion 110' and back wall 218.

As with the other embodiments, line lock 200 can be slid along line 100 and/or line 100 can be pulled therethrough so as to remove all unwanted slack from standing portion 102. As line 100 is tension on line lock 200, compression portions 110 and 110' force the portion of line 100 extending between first working passageways 228 and 228' and between second working passageways 230 and 230', respectively, toward corresponding capture slots 34. As a result, at least a portion of line 100 extending through each of the working passageways is captured by frictional wedge engagement within each of the corresponding capture slots 34. Line 100 is thus locked with line lock 200.

Line lock 200 offers several advantages. When standing end 102 is slack and working ends 104 and 104' are tensioned, the sections of line 100 extending between working passageways 228 and 228' and between working passageways 230 and 230' force compression portions 110 and 110', respectively, back toward front wall 216 so as to allow the free travel of line 100 through line lock 200. In contrast, as discussed above, when tension is created in standing end 102 and slack is created in working ends 104 and 104', compression portions 110 and 110' force the sections of line 100 extending between working passageways 228 and 228' and between working passageways 230 and 230' toward back wall 218 so as to secure line 100 within the capture slots 34. This back and forth movement of compression portions 110 and 110' creates "backlash," or a finite distance that line lock 200 can move away from standing end 102 until locking of line 100 is achieved.

Top wall 204 of line lock 200 provides a physical constraint to the amount of movement seen in compression portions 110 and 110', thereby minimizing the amount of backlash. Furthermore, top wall 204 provides an additional friction point when compression portions 110 and 110' compress against line 100, thereby increasing the strength of the locking of line 100. That is, one friction point is located at working passageways 228 and 230 on bottom wall 206 and the second friction point is located at working passageways 228' and 230' on top wall 204.

It is again appreciated that the alternatives as discussed with the other embodiments are also applicable to line lock 200. By way of example and not by limitation, line 100 can be routed through line lock 200 in a manner analogous to the routing in FIG. 7. The various passageways can be open or closed as depicted in FIGS. 8 and 9. Similarly, line lock 200 can be divided in half and modified to function similar to the line locks shown in FIGS. 11–14.

Figure 17:
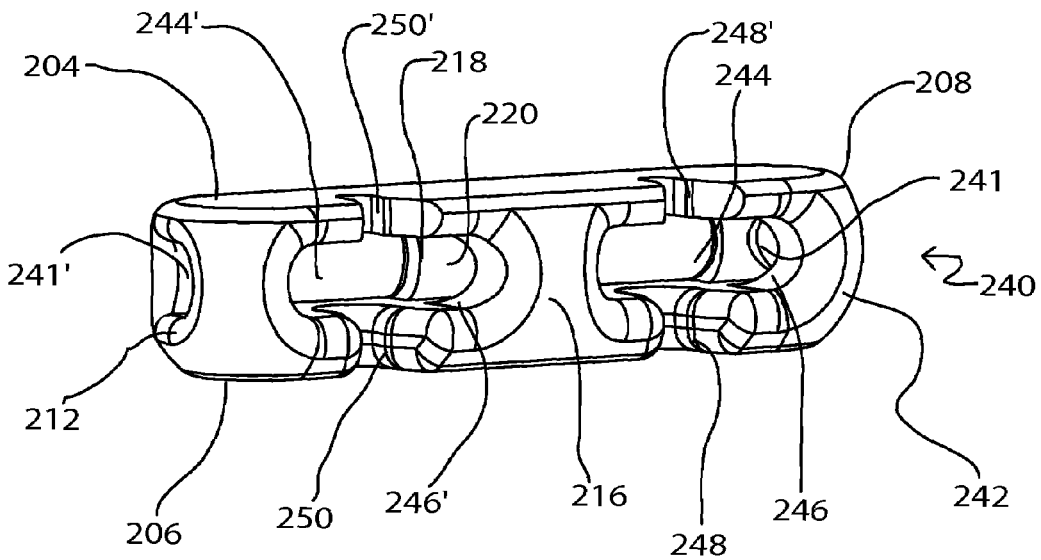
FIG. 17 is a perspective view of another alternative embodiment of a line lock.

Depicted in FIG. 17 is a final alternative embodiment of a line lock 240 incorporating features of the present invention. Line lock 240 has a configuration similar to line lock 200 and thus like elements are identified by like reference characters. Line lock 240 comprises an elongated substantially box shaped body 242. Similar to line lock 200, body 242 comprises top wall 204 and bottom wall 206 extending between side wall 208 and side wall 212. Body 242 also includes front wall 216 and back wall 218 which partially bound chamber 220.

In contrast to line lock 200, a first primary passageway 241 extends through first side wall 208 while second primary passageway 241' extends through second side wall 212. Primary passageways 241 and 241' each communicate with chamber 220. Body 242 of line lock 240 further comprises a first secondary passageway 244 extending through back wall 218 in communication with chamber 220 and a spaced apart second secondary passageway 244' in communication with chamber 220. A first access port 246 extends through front wall 216 in alignment with first secondary passageway 244' so as to communicate with chamber 220. Similarly, a second access port 246' extends through front wall 216 in alignment with second secondary passageway 244 so as to also communicate with chamber 220.

Furthermore, in contrast to the bounded working passageways of line lock 200, line lock 240 comprises a pair of first working passageways 248 and 248'. Working passageway 248 comprises a constricting slot that is formed on bottom wall 206 and is open along intersecting front wall 216. First working passageway 248' is aligned with first working passageway 248 and is formed on top wall 204 so as to also be open along intersecting front wall 216. A pair of second working passageways 250 and 250' are similarly formed on bottom wall 206 and top wall 204 so as to be aligned with second secondary passageway 244'. Each of the working passageways terminates at capture slot having a width substantially equal to or smaller than the diameter of line 100.

Figure 18A:
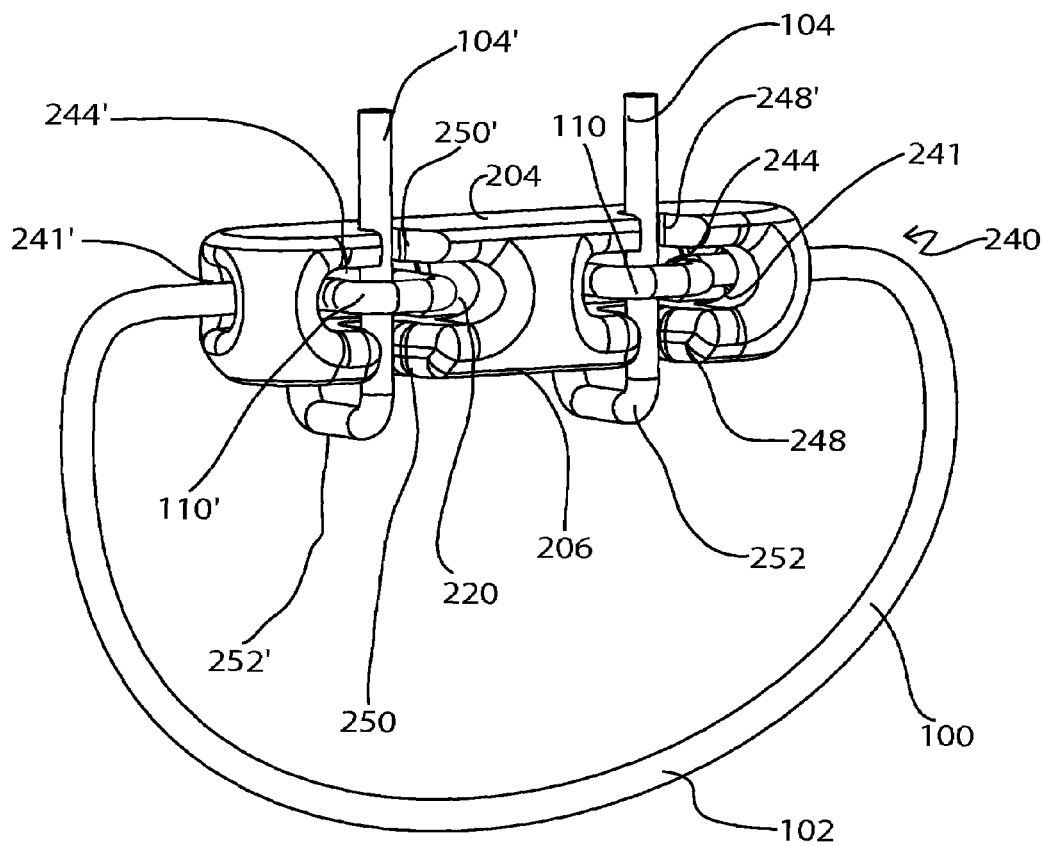
FIG. 18A is a perspective view of the line lock shown in FIG. 17 with a line routed therethrough.
Figure 18B:
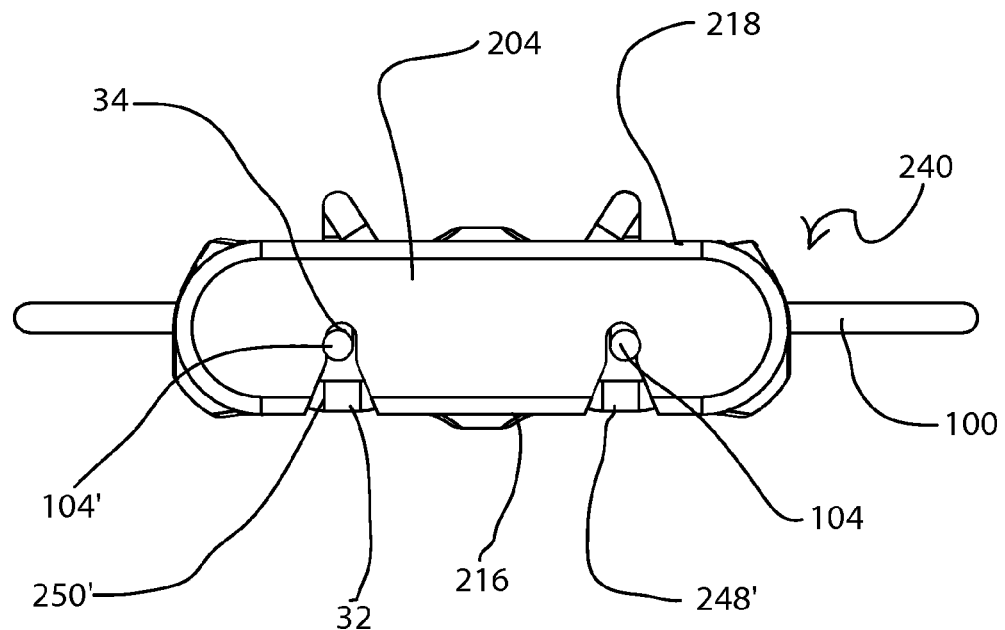
FIG. 18B is a top plan view of the line lock shown in FIG. 18A.
Figure 18C:
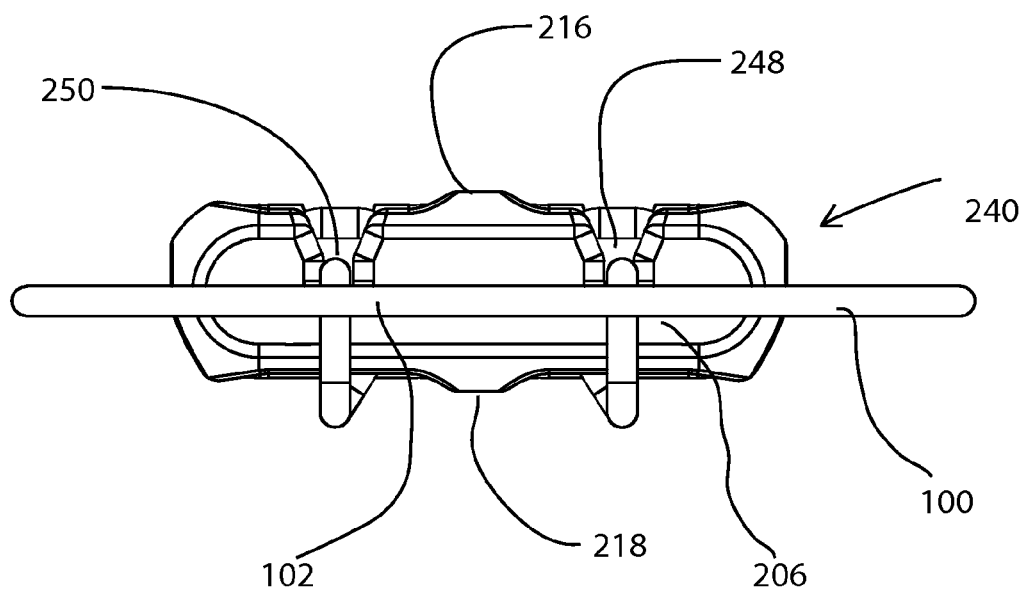
FIG. 18C is a bottom plan view of the line lock shown in FIG. 18A.

During use, as depicted in FIGS. 18A–18C, working end 104 of line 100 is passed through first primary passageway 242 into chamber 220 and then out through first secondary passageway 244. Working end 104 then passes down around bottom wall 206 and is then fed up through first working passageways 248 and 248'. A compression portion 110 of line 100 extends between primary passageway 241 and secondary passageway 244. Working portion 104 is passed between working passageways 248, 248' so that line 100 passes between compression portion 110 and first secondary passageway 244.

Working portion 104' is similarly passed through the passageways on the opposing side of line lock 240. That is, working portion 104' passes through primary passageway 241' and into chamber 220. Working portion 104' then travels out through secondary passageway 244', bends around bottom wall 206, and then travels up through working passageways 250 and 250'.

In the above configuration, slack can be removed from standing portion 102 by pulling line 100 through line lock 240 and/or sliding line lock 240 toward standing portion 102. As line 100 tensions on line lock 240, compression portions 110 and 110' again force portions of line 100 into capture slots 34 of the working passageways so as to secure line 100 to line lock 240 by wedged frictional engagement.

Like line lock 200, line lock 240 provides containment of compression portions 110 and 110' to minimize backlash. Unlike the other embodiments, line 100 is routed through line lock 240 such that at least one line turn exceeds 90 degrees. For example, the transition between compression portions 110 and 110' and looping portions, designated as 252 and 252', respectively, create 180 degree turns in line 100 These sharp bends in line 100 increase the friction that must be overcome in order to advance line lock 240 toward standing end 102. However, the sharp bends also contribute to greater locking strength of line lock 240 to line 100. This embodiment is beneficial when line 100 is monofilament or single strand line, due to the commonly lower line on line friction and greater flexural stiffness of monofilament line when compared to braided or twisted strand line.

While the present invention has application to any need for securing a line, it is particularly advantages to surgical suture applications as a way to conveniently and reliable replace the need to tie suture knots. The advantage is even greater in anthroscopic and endoscopic applications, where sophisticated sliding knots followed by "back-up" knots must be tied outside of a cannula and slid into final position at an internal body site. The sophisticated sliding knots are difficult to tie, time consuming, and bulky. The present invention provides an easy to apply, quick to deliver, and low profile solution that will reliably maintain the desired suture tension.

The present invention may be embodied in other specific forms without departing from its spirit or essential characteristics. For example, above are described various alternative examples of different adjustable line locks. It is appreciated that various features of the line locks can be mixed and matched to form a variety of other alternatives. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A line lock comprising a body at least partially bounding a first primary passageway, a first secondary passageway, and a first working passageway, the first working passageway having a transverse cross sectional area with a first location having a first minimum width and a spaced apart second location having a second minimum width that is smaller than the first minimum width, at least a portion of the first working passageway being disposed between the first primary passageway and the first secondary passageway such that a geometric line segment extending between the first primary passageway and the first secondary passageway intersects with first working passageway, wherein the body is comprised of a bioabsorbable material.

2. A line lock as recited in claim 1, wherein the body further at least partially bounds an end passageway, the end passageway and the first working passageway being positioned such that they can each be intersected by a common plane disposed between but not intersecting with the first primary passageway and the first secondary passageway.

3. A line lock as recited in claim 1, wherein the body further at least partially bounds a second secondary passageway and a second working passageway, the second working passageway having a transverse cross sectional area with a first location having a first minimum width and a spaced apart second location having a second minimum width that is smaller than the first minimum width, at least a portion of the second working passageway being disposed between the first primary passageway and the second secondary passageway.

4. A line lock as recited in claim 3, wherein the portion of the second working passageway is disposed between the first primary passageway and the second secondary passageway such that a geometric line segment extending between the first primary passageway and the second secondary passageway intersects with the second working passageway.

5. A line lock as recited in claim 3, further comprising a line, the line comprising:
  a first portion extending through the first primary passageway, the first secondary passageway, and the first working passageway; and
  a second portion extending through the first primary passageway, the second secondary passageway, and the second working passageway, the second portion being spaced apart from the first portion.

6. A line lock as recited in claim 1, wherein the body at least partially bounds a second primary passageway.

7. A line lock as recited in claim 1, wherein the body has a maximum dimension of less than about 1.5 cm.

8. A line lock as recited in claim 1, wherein the first primary passageway, the first secondary passageway, and the first working passageway each comprise a corresponding bounded aperture.

9. A line lock as recited in claim 1, further comprising a line extending through the first primary passageway, the first secondary passageway, and the first working passageway, the line having a maximum diameter larger than the second minimum width of the second location of the first working passageway.

10. A line lock as recited in claim 9, wherein at least a portion of the line is permanently secured to the body.

11. A line lock as recited in claim 1, wherein the body comprises a top wall and an opposing bottom wall which at least partially bound a chamber therebetween.

12. A line lock comprising a body, the body at least partially bounding:
  a first working passageway having a transverse cross sectional area that is elongated and extends between a first end and an opposing second end;
  a first primary passageway disposed on one side of the first working passageway, the first primary passageway being bounded by an interior surface which includes a side face disposed towards the first working passageway, the side face being substantially disposed in or tangent to a first plane; and
  a first secondary passageway disposed on a side of the first working passageway opposite the first primary passageway, the first secondary passageway being bounded by an interior surface which includes a side face disposed towards the first working passageway, the side face being substantially disposed in or tangent to a second plane, wherein the first plane and the second plane are disposed so as to be converging as they extend toward the first end of the transverse cross sectional area of the first working passageway.

13. A line lock as recited in claim 12, wherein at least a portion of the first working passageway is directly disposed between the first primary passageway and the first secondary passageway such that a geometric line segment extending between the first primary passageway and the first secondary passageway intersects with first working passageway.

14. A line lock as recited in claim 12, wherein the first end of the transverse cross sectional area of the first working passageway has a first minimum diameter and the second end of the transverse cross sectional area of the first working passageway has a second minimum diameter that is larger than the first minimum diameter.

15. A line lock as recited in claim 12, wherein the body further at least partially bounds an end passageway, the end passageway and the first working passageway being positioned such that they can each be intersected by a common plane disposed between but not intersecting with the first primary passageway and the first secondary passageway.

16. A line lock as recited in claim 12, wherein the body further at least partially bounds a second secondary passageway and a second working passageway, the second working passageway having a transverse cross sectional area with a first location having a first minimum width and a spaced apart second location having a second minimum width that is smaller than the first minimum width, at least a portion of the second working passageway being disposed between the first primary passageway and the second secondary passageway.

17. A line lock as recited in claim 16, wherein the portion of the second working passageway is disposed between the first primary passageway and the second secondary passageway such that a geometric line segment extending between the first primary passageway and the second secondary passageway intersects with the second working passageway.

18. A line lock as recited in claim 12, wherein the body has a maximum dimension of less than about 1 cm.

19. A line lock as recited in claim 12, wherein the first primary passageway and the first secondary passageway each comprise a corresponding bounded aperture.

20. A line lock as recited in claim 12, further comprising a line extending through the first primary passageway, the first secondary passageway, and the first working passageway.

21. A line lock comprising:
  a body at least partially bounding a first primary passageway, a first secondary passageway, and a first working passageway, the first working passageway extending between a top working opening bounded by an outside corner and a bottom working opening bounded by an outside corner; and
  a line extending through the first primary passageway or the first secondary passageway and then through the other of the first primary passageway or the first secondary passageway such that a relative compression section of the line is formed between the first primary passageway and the first secondary passageway, the line then extending through the first working passageway so as to pass over a portion of the outside corner of bottom working opening having a first radius of curvature and to pass over a portion of the outside corner of the top working opening having a second radius of curvature, the first radius of curvature being greater than the second radius of curvature.

22. A line lock as recited in claim 21, wherein at least a portion of the first working passageway is directly disposed between the first primary passageway and the first secondary passageway such that a geometric line segment extending between the first primary passageway and the first secondary passageway intersects with the first working passageway.

23. A line lock as recited in claim 21, wherein the first working passageway has a transverse cross sectional area with a first location having a first minimum width and a spaced apart second location having a second minimum width that is smaller than the first minimum width.

24. A line lock as recited in claim 21, wherein the body further at least partially bounds an end passageway having the line extending therethrough.

25. A line lock as recited in claim 21, wherein the body further at least partially bounds a second secondary passageway and a second working passageway, the second working passageway having a transverse cross sectional area with a first location having a first minimum width and a spaced apart second location having a second minimum width that is smaller than the first minimum width, at least a portion of the second working passageway being disposed between the first primary passageway and the second secondary passageway.

26. A line lock as recited in claim 25, wherein the portion of the second working passageway is disposed between the first primary passageway and the second secondary passageway such that a geometric line segment extending between the first primary passageway and the second secondary passageway intersects with the second working passageway.

27. A line lock as recited in claim 21, wherein the body has a maximum dimension of less than about 2 cm.

28. A line lock as recited in claim 21, wherein at least one of the first primary passageway, first secondary passageway, and first working passageway comprise an open channel.

29. A line lock as recited in claim 21, wherein at least a portion of the line is permanently secured to the body.

30. A line lock as recited in claim 21, wherein the first radius of curvature is in a range between about 0.5 mm to about 1.5 mm and the second radius of curvature is in a range between about 0 mm to about 0.5 mm.

31. A line lock comprising:
a body having a top surface and an opposing bottom surface;
a first primary passageway extending between a top primary opening at least partially bounded by an outside corner on the top surface of the body and bottom primary opening at least partially bounded by an outside corner on the bottom surface of the body;
a first secondary passageway extending between a top secondary opening at least partially bounded by an outside corner on the top surface of the body and a bottom secondary opening at least partially bounded by an outside corner on the bottom surface of the body; and
a first working passageway extending between a top working opening at least partially bounded by an outside corner on the top surface of the body and a bottom working opening at least partially bounded by an outside corner on the bottom surface of the body, wherein at least a section of the outside corner of the top primary opening, top secondary opening, or top working opening has a radius of curvature that is smaller than a radius of curvature of at least a section of the outside corner of the bottom primary opening, bottom secondary opening, or bottom working opening.

32. A line lock as recited in claim 31, wherein at least a portion of the first working passageway is directly disposed between the first primary passageway and the first secondary passageway such that a geometric line segment extending between the first primary passageway and the first secondary passageway intersects with the first working passageway.

33. A line lock as recited in claim 31, wherein the first working passageway has a transverse cross sectional area with a first location having a first minimum width and a spaced apart second location having a second minimum width that is smaller than the first minimum width.

34. A line lock as recited in claim 31, wherein the body further at least partially bounds an end passageway having the line extending therethrough.

35. A line lock as recited in claim 31, wherein the body further at least partially bounds a second secondary passageway and a second working passageway, the second working passageway having a transverse cross sectional area with a first location having a first minimum width and a spaced apart second location having a second minimum width that is smaller than the first minimum width, at least a portion of the second working passageway being disposed between the first primary passageway and the second secondary passageway.

36. A line lock as recited in claim 31, wherein the body has a maximum dimension of less than about 2 cm.

37. A line lock as recited in claim 31, wherein at least one of the first primary passageway, first secondary passageway, and first working passageway comprise an open channel.

38. A line lock as recited in claim 31, wherein at least a portion of the line is permanently secured to the body.

39. A line lock comprising:
a body at least partially bounding a first primary passageway, a first secondary passageway, and a first working passageway, the first working passageway having a transverse cross sectional area with a first location having a first minimum width and a spaced apart second location having a second minimum width that is smaller than the first minimum width; and
a line extending through the first primary passageway or the first secondary passageway and then through the other of the first primary passageway or the first secondary passageway such that a relative compression section of the line is formed between the first primary passageway and the first secondary passageway, the line then extending through the first working passageway, wherein the first primary passageway, the first secondary passageway, and the first working passageway are oriented such that the compression section of the line presses at least a portion of the line extending through the first working passageway into the second location of the transverse cross sectional area of the first working passageway when at least a portion of the line is tensioned against the body.

40. A line lock as recited in claim 39, wherein at least a portion of the first working passageway is directly disposed between the first primary passageway and the first secondary passageway such that a geometric line segment extending between the first primary passageway and the first secondary passageway intersects with the first working passageway.

41. A line lock as recited in claim 39, wherein the body further at least partially bounds an end passageway, the line passing through the end passageway prior to or after passing through the first primary passageway and the first secondary passageway.

42. A line lock as recited in claim 39, wherein the body further at least partially bounds a second secondary passageway and a second working passageway, the second working passageway having a transverse cross sectional area with a first location having a first minimum width and a spaced apart second location having a second minimum width that is smaller than the first minimum width, at least a portion of the second working passageway being disposed between the first primary passageway and the second secondary passageway, the line passing through the second secondary passageway and the second working passageway.

43. A line lock as recited in claim 42, wherein the portion of the second working passageway is disposed between the first primary passageway and the second secondary passageway such that a geometric line segment extending between the first primary passageway and the second secondary passageway intersects with the second working passageway.

44. A line lock as recited in claim 39, wherein the body has a maximum dimension of less than about 2 cm.

45. A line lock as recited in claim 39, wherein at least two of the first primary passageway, first secondary passageway, and first working passageway comprise a corresponding bounded aperture.

46. A line lock as recited in claim 39, wherein at least a portion of the line is permanently secured to the body.

47. A line lock comprising:
a body at least partially bounding a first primary passageway, a first secondary passageway, and a first working passageway, the first working passageway having a top working opening bounded by an outside corner; and
a line extending through the first primary passageway or the first secondary passageway and then through the other of the first primary passageway or the first secondary passageway such that a relative compression section of the line is formed between the first primary passageway and the first secondary passageway, the line then extending through the first working passageway, wherein the first primary passageway, the first secondary passageway, and the first working passageway are oriented such that the compression section of the line directly presses the line extending through the first working passageway against the outside corner of the top working opening when at least a portion of the line is tensioned against the body.

48. A line lock as recited in claim 47, wherein the compression section of the line passes over at least a portion of the first working passageway when the line is tensioned against the body.

49. A line lock as recited in claim 47, wherein the first working passageway has a transverse cross sectional area with a first location having a first minimum width and a spaced apart second location having a second minimum width that is smaller than the first minimum width.

50. A line lock as recited in claim 49, wherein the compression section of the line presses at least a portion of the line extending through the first working passageway into the second location of the transverse cross sectional area of the first working passageway when at least a portion of the line is tensioned against the body.

51. A line lock as recited in claim 47, wherein at least a portion of the first working passageway is directly disposed between the first primary passageway and the first secondary passageway such that a geometric line segment extending between the first primary passageway and the first secondary passageway intersects with first working passageway.

52. A line lock as recited in claim 47, wherein the body further at least partially bounds an end passageway, the line passing through the end passageway prior to or after passing through the first primary passageway and the first secondary passageway.

53. A line lock as recited in claim 47, wherein the body further at least partially bounds a second secondary passageway and a second working passageway, the second working passageway having a transverse cross sectional area with a first location having a first minimum width and a spaced apart second location having a second minimum width that is smaller than the first minimum width, at least a portion of the second working passageway being disposed between the first primary passageway and the second secondary passageway, the line passing through the second secondary passageway and the second working passageway.

54. A line lock as recited in claim 47, wherein at least two of the first primary passageway, first secondary passageway, and first working passageway comprise a corresponding bounded aperture.

55. A line lock as recited in claim 47, wherein at least a portion of the line is permanently secured to the body.

56. A line lock comprising:
a body at least partially bounding a first primary passageway, a first secondary passageway, and a first working passageway, at least a portion of the first working passageway being disposed between the first primary passageway and the first secondary passageway such that a geometric line segment extending between the first primary passageway and the first secondary passageway intersects with first working passageway; and
a line extending through the first primary passageway or the first secondary passageway and then through the other of the first primary passageway or the first secondary passageway such that a relative compression section of the line is formed between the first primary passageway and the first secondary passageway, the line then extending through the first working passageway, the compression section of the line selectively biasing against a portion of the line extending out of the first working passageway so as to selectively lock the line to the body.

57. A line lock as recited in claim 56, wherein the compression section of the line passes over at least a portion of the first working passageway.

58. A line lock as recited in claim 56, wherein the first working passageway has a transverse cross sectional area with a first location having a first minimum width and a spaced apart second location having a second minimum width that is smaller than the first minimum width.

59. A line lock as recited in claim 58, wherein the compression section of the line presses at least a portion of the line extending through the first working passageway into the second location of the transverse cross sectional area of the first working passageway.

60. A line lock as recited in claim 58, wherein the line has a maximum diameter larger than the second minimum width of the second location of the first working passageway.

61. A line lock as recited in claim 56, wherein the body further at least partially bounds a second secondary passageway and a second working passageway, the second working passageway having a transverse cross sectional area with a first location having a first minimum width and a spaced apart second location having a second minimum width that is smaller than the first minimum width, at least a portion of the second working passageway being disposed between the first primary passageway and the second secondary passageway, the line passing through the second secondary passageway and the second working passageway.

62. A method of locking a line, the method comprising:
- passing a line through a first passageway of a line lock, through a second passageway of a line lock, and through a working passageway of a line lock such that a compression section of the line extends between the first passageway and the second passageway, the working passageway comprising a constricted capture slot having a width smaller than a maximum diameter of the line;
- passing the line through a third passageway on the line lock; and
- tensioning at least a portion of the line such that the compression section of the line biases a section of the line extending through the working passageway into the capture slot.

63. A method of locking a line, the method comprising:
- providing a line lock having a first surface, a second surface, first corners disposed on a first surface, second corners disposed on a second surface, at least one of the first corners having a radius of curvature that is smaller than a radius of curvature of at least one of the second corners, and passageways extending between the first corners and the second corners;
- passing a relative locking portion of a line through the passageways, the line comprising a relative standing portion, a relative working portion, and the relative locking portion extending therebetween; and
- tensioning one of the standing portion or the working portion so that the locking portion biases against the working portion and a portion of the line also biases against at least one of the first corners which has a radius of curvature smaller than a radius of curvature of at least one of the second corners.

* * * * *

UNITED STATES PATENT AND TRADEMARK OFFICE
CERTIFICATE OF CORRECTION

| | | |
|---|---|---|
| PATENT NO. | : 7,150,757 B2 | Page 1 of 3 |
| APPLICATION NO. | : 10/459375 | |
| DATED | : December 19, 2006 | |
| INVENTOR(S) | : T. Wade Fallin et al. | |

It is certified that error appears in the above-identified patent and that said Letters Patent is hereby corrected as shown below:

- Column 1. Line 60. (Background of the Invention) should read:
--applications, a free-[[device ]]floating device such as a line lock can--

- Column 2. Line 9. (Brief Description of Drawings) should read:
--FIG. 2 is a top plan view of the line lock shown in FIG. 1;--

- Column 5. Line 27. (Detailed Description) should read:
--between about 0.7 mm to 1 mm while capture slots ~~17~~ 34 have--

- Column 5. Line 33. (Detailed Description) should read:
--corner ~~66~~ 68 bounds a bottom primary opening 72. Similarly,--

- Column 5. Line 37. (Detailed Description) should read:
--working opening 80 while bottom ouside corner ~~76~~ 78 bounds--

- Column 5. Line 42. (Detailed Description) should read:
--bottom outside corner ~~86~~ 88 bounds a bottom secondary opening 92.--

- Column 5. Line 65. (Detailed Description) should read:
--and second working passageway 28' ~~having~~ have substantially the--

- Column 6. Line 5. (Detailed Description) should read:
--line lock 12 ~~10~~. Line 100 comprises a standing portion 102 in--

- Column 6. Line 33. (Detailed Description) should read:
--line lock ~~110~~ 10. In either event, at least one of working--

- Column 6. Line 59. (Detailed Description) should read:
toward ~~first~~ second side 21 of body 12.--

- Column 8. Line 32. (Detailed Description) should read:
outside corners 66 and 86 are formed ~~relative~~ relatively sharp as--

- Column 8. Line 66. (Detailed Description) should read:
--greater than the diameter of line 110. Second end 126 extends--

UNITED STATES PATENT AND TRADEMARK OFFICE
CERTIFICATE OF CORRECTION

PATENT NO. : 7,150,757 B2
APPLICATION NO. : 10/459375
DATED : December 19, 2006
INVENTOR(S) : T. Wade Fallin et al.

It is certified that error appears in the above-identified patent and that said Letters Patent is hereby corrected as shown below:

- Column 10. Line 54. (Detailed Description) should read:
--tissue. By pulling on working portion 104 of suture, the ~~tom~~ torn--

- Column 10. Line 56. (Detailed Description) should read:
--line lock 150 maintains the ~~tom~~ torn tissue adjacent to the normal--

- Column 12. Line 11. (Detailed Description) should read:
--passageway 224 centrally extends through bottom wall 206 to--

- Column 13. Line 46. (Detailed Description) should read:
--secondary passageway ~~244~~' 244 so as to communicate with--

- Column 13. Line 49. (Detailed Description) should read:
--passageway ~~244~~ 244' so as to communicate with chamber--

- Column 13. Line 67. (Detailed Description) should read:
--~~242~~ 241 into chamber 220 and then out through first secondary--

- Column 14. Line 30. (Detailed Description) should read:
--100. These sharp bends in line 100 increase the friction that--

- Column 14. Line 39. (Detailed Description) should read:
--for securing a line, it is particularly ~~advantages~~ advantageous to surgical--

- Column 14. Line 40. (Detailed Description) should read:
--suture applications as a way to conveniently and ~~reliable~~ reliably--

UNITED STATES PATENT AND TRADEMARK OFFICE
CERTIFICATE OF CORRECTION

PATENT NO. : 7,150,757 B2
APPLICATION NO. : 10/459375
DATED : December 19, 2006
INVENTOR(S) : T. Wade Fallin et al.

It is certified that error appears in the above-identified patent and that said Letters Patent is hereby corrected as shown below:

- Column 14. Line 42. (Detailed Description) should read:
--greater in ~~anthroscopic~~ arthroscopic and endoscopic applications, where--

- Column 20. Line 37. (Claim 56) should read:
--passageway intersects with the first working passageway; and--

Signed and Sealed this

Fifth Day of February, 2008

JON W. DUDAS
*Director of the United States Patent and Trademark Office*